US007927850B2

(12) United States Patent
Shaw et al.

(10) Patent No.: US 7,927,850 B2
(45) Date of Patent: Apr. 19, 2011

(54) COMPOSITION CONTAINING TREHALOSE SYNTHASE AND METHODS OF USE THEREOF

(75) Inventors: Jei-Fu Shaw, Taipei (TW); Guan-Chiun Lee, Taipei (TW); Yi-Shan Chen, Taichung (TW)

(73) Assignee: Academia Sinica, Taipei (TW)

( * ) Notice: Subject to any disclaimer, the term of this patent is extended or adjusted under 35 U.S.C. 154(b) by 750 days.

(21) Appl. No.: 11/490,702

(22) Filed: Jul. 21, 2006

(65) Prior Publication Data

US 2008/0182311 A1    Jul. 31, 2008

(51) Int. Cl.
*C12N 9/00* (2006.01)
*C12N 1/20* (2006.01)
*C12N 15/00* (2006.01)
*C07H 21/04* (2006.01)

(52) U.S. Cl. .................. 435/183; 435/252.3; 435/320.1; 536/23.2

(58) Field of Classification Search ........................ None
See application file for complete search history.

(56) References Cited

U.S. PATENT DOCUMENTS 5,312,739 A    5/1994 Shaw
5,643,758 A *  7/1997 Guan et al. ................... 435/69.7
2004/0043953 A1* 3/2004 Pompejus et al. ............. 514/44

OTHER PUBLICATIONS

Accession Q6L227, published Jul. 5, 2004.*
Accession AE017261, published Jun. 9, 2004.*
Alignment of AXK03448 to SEQ ID No. 4. From WO2006069610-A2, published Jul. 6, 2006.*
Alignment of AXK03448 to SEQ ID No. 2. From WO2006069610-A2, published Jul. 6, 2006.*
Alignment of AXK03448 to SEQ ID No. 1. From WO2006069610-A2, published Jul. 6, 2006.*
Alignment of AE017261 to SEQ ID No. 4. Accession AE017261. published Jun. 9, 2004.*
Alignment of AE017261 to SEQ ID No. 2. Accession AE017261. published Jun. 9, 2004.*
Elbein, A. D., et al. New insights on trehalose: a multifunctional molecule. Glycobiology 2003, 13, 17-27.
Brennan, P. J., et al. The envelope of mycobacteria. Annu. Rev. Biochem. 1995, 64, 29-63.
Puech, V. et al. Structure of the cell envelope of corynebacteria . . . . Microbiology 2001, 147, 1365-1382.
Eastmond, P. J., et al. Trehalose metabolism: a regulatory role for trehalose-6-phosphate? Curr. Opin. Plant Biol. 2003, 6, 231-235.
Gancedo, C., et al. The importance of a functional trehalose biosynthetic pathway for the life of yeasts and fungi. FEMS Yeast Res. 2004, 4, 351-359.
Wingler, A. et al. Trehalose induces the ADP-glucose pyrophosphorylase gene, ApL3, and starch synthesis in *Arabidopsis*. Plant Physiol. 2000, 124, 105-114.

Chen, Q. et al. Expression of *Drosophila* trehalose-phosphate synthase in HEK-293 cells increases hypoxia tolerance. J. Biol. Chem. 2003, 278, 49113-49118.
Kandror, O., et al. Trehalose synthesis is induced upon exposure of *Escherichia coli* to cold . . . . Proc. Natl. Acad. Sci. U.S.A. 2002, 99, 9727-9732.
Purvis, J. et al. Enhanced trehalose production improves growth of *Escherichia coli* under osmotic stress. Appl. Environ. Microbiol. 2005, 71, 3761-3769.
Benaroudj, N., et al. Trehalose accumulation during cellular stress protects cells and cellular proteins from damage by oxygen radicals. J. Biol. Chem. 2001, 276, 24261-24267.
Welch, W. J., et al. Influence of molecular and chemical chaperones on protein folding. Cell Stress Chaperones 1996, 1, 109-115.
Schiraldi, C., et al. Trehalose production: exploiting novel approaches. Trends Biotechnol. 2002, 20, 420-425.
Cabib, E., et al. The biosynthesis of trehalose phosphate. J. Biol. Chem. 1958, 231, 259-275.
Maruta, K., et al. Formation of trehalose from maltooligosaccharides by a novel enzymatic system. Biosci. Biotechnol. Biochem. 1995, 59, 1829-1834.
Nakada, T., et al. Purification and properties of a novel enzyme, maltooligosyl trehalose synthase . . . . Biosci. Biotechnol. Biochem. 1995, 59, 2210-2214.
Nakada, T., et al. Purification and characterization of a novel enzyme, maltooligosyl trehalose trehalohydrolase . . . . Biosci. Biotechnol. Biochem. 1995, 59, 2215-2218.
Nishimoto, T., et al. Existence of a novel enzyme converting maltose into trehalose. Biosci. Biotechnol. Biochem. 1995, 59, 2189-2190.
Nishimoto, T., et al. Purification and properties of a novel enzyme, trehalose sythase, from *Pimelobacter* sp. R48. Biosci. Biotechnol. Biochem. 1996, 60, 640-644.
Nishimoto, T., et al. Purification and charaterization of a thermostable trehalose synthase from *Thermus aquaticus*. Biosci. Biotechnol. Biochem. 1996, 60, 835-839.
Koh, S., et al. Trehalose synthesis from maltose by a thermostable trehalose synthase from *Thermus caldophilus*. Biotechnology Letters 1998, 20, 757-761.
Pan, Y. T., et al. Trehalose synthase of *Mycobacterium smegmatis*: purification, cloning, expression and properties of the enzyme. Eur. J. Biochem. 2004, 271, 4259-4269.
Wei, Y. T., et al. Cloning, expression and identification of a new trehalose synthase gene from *Thermobifida fusca* genome. Acta Biochim. Biophys. Sin. 2004, 36, 477-484. Lee, J. H., et al. Cloning and expression of a trehalose synthase from *Pseudomonas stutzeri* CJ38 in *Escherichia coli* . . . . Appl. Microbiol. Biotechnol. 2005, 68, 213-219.
Futterer, O., et al. Genome sequence of *Picrophilus torridus* and its implications for life around pH 0. Proc. Natl. Acad. Sci. U.S.A. 2004, 101, 9091-9096.
Watanabe, K., et al. Identification of catalytic and substrate-binding site residues in *Bacillus cereus* . . . . Biosci. Biotechnol. Biochem. 2001, 65, 2058-2064.

(Continued)

*Primary Examiner* — Christian L Fronda

(57) ABSTRACT

The present invention relates to the isolation and functional identification of a novel acid and heat resistant trehalose synthase enzyme cloned from *Picrophilus torridus*. More particularly, the present invention discloses the DNA sequence for the *Picrophilus torridus* trehalose synthase gene, PTTS, which when expressed in a heterologous host such as *Escherichia coli*, provides enzymatic activity that catalyzes the direct interconversion of maltose and trehalose through intramolecular transglycosylation. Additionally, the present invention teaches methods of use of PTTS for production of trehalose as well as for production of various useful compounds comprising trehalose.

10 Claims, 7 Drawing Sheets

OTHER PUBLICATIONS

Zhang, D., et al. Isomaltulose synthase (PalI) of *Klebsiella* sp. LX3. Crystal structure and implication of mechanism. J. Biol. Chem. 2003, 278, 35428-35434.

Dworschak, E. Nonenzyme browning and its effect on protein nutrition. Crit. Rev. Food. Sci. Nutr. 1980, 13, 1-40.

Fennema, O. R. Carbohydrates. In Food Chemistry, 2nd ed.; Marcel Dekker, Inc.: New York, 1985; pp. 96-105.

MacGregor, E. A., et al. Relationship of sequence and structure to specificity in the alpha-amylase family of enzymes. Biochim. Biophys. Acta. 2001, 1546,1-20.

Koh, S., et al. Mechanistic study of the intramolecular conversion of maltose to trehalose by *Thermus caldophilus* . . . . Carbohydr. Res. 2003, 338, 1339-1343.

Shaw, J.F., et al. Production of high-maltose syrup and high-protein flour from rice by an enzymatic method. Biosci. Biotechnol. Biochem. 1992, 56, 1071-1073.

* cited by examiner

Table 1. Kinetic Parameters of PTTS.

| Substrate | $K_M$ (mM) | $V_{max}{}^a$ (μmol/min·μmol) | $k_{cat}$ (s$^{-1}$) | $k_{cat}/K_M$ (M$^{-1}$·s$^{-1}$) |
|---|---|---|---|---|
| Maltose | 42.4±1.6 | 5699.4±61.4 | | 2238.1±108.1 |
| Trehalose | 210.3±3.9 | 11257.3±295.1 | 95.0±1.0 | 892.1±6.9 |
| Maltose + 10 mM Glucose | 137.8±4.0 | 5870.1±120.7 | 187.6±5. | 709.8±6.4 |

$^a$ The concentration of purified PTTS used was 0.38 μM. The theoretical molecular weight of the recombinant PTTS is 68016.

Figure 8

Table 2. Effects of Metal Ions and Reagents on the Activity of PTTS.

| Reagent | Relative Activity$^a$ (%) | |
|---|---|---|
| | 1 mM | 10 mM |
| None | 100 | 100 |
| MnCl2 | 108 | 0 |
| CsCl | 106 | 89 |
| ZnSO$_4$ | 102 | 0 |
| MgCl2 | 99 | 7 |
| SrCl2 | 98 | 4 |
| CaCl$_2$ | 97 | 4 |
| LiCl | 96 | 89 |
| CoCl$_2$ | 96 | 1 |
| BaSO$_4$ | 93 | 4 |
| NiCl$_2$ | 90 | 3 |
| FeSO$_4$ | 84 | 0 |
| FeCl3 | 80 | 0 |
| CdSO$_4$ | 64 | 0 |
| CuSO$_4$ | 62 | 0 |
| PbCl2 | 60 | 62 |
| AgNO3 | 0 | 0 |
| HgCl2 | 0 | 0 |
| Al$_2$(SO$_4$)$_3$ | 0 | 0 |
| DTT | 96 | 85 |
| EDTA | 93 | 85 |
| Tris | 67 | 8 |
| SDS | 0 | 0 |

$^a$ Enzyme activity was measured in the presence of 1mM and 10 mM metal ions or reagents under assay conditions of temperature 45 °C, 50mM sodium phosphate buffer (pH 6.0) and 150mM maltose for 25min. Relative activity (%) was expressed as a percentage of the enzyme activity in the absence of metal ions and reagents.

Figure 9

Table 3. Relative Specific Activity of Wild-type PTTS and its Mutant Enzymes.

| Mutation | Relative specific activity[a] (%) |
|---|---|
| Wild-type | 100 |
| H106A | 0.73±0.115 |
| D203A | 0.21±0.005 |
| E245A | 0.26±0.007 |
| H310A | 10.95±0.144 |
| D311A | 0.20±0.034 |

[a] Relative activities (%) are represented as the ratio of mutants to wild type. The specific activity of wild-type PTTS was 86 units/mg.

SEQUENCE LISTING

```
<160> NUMBER OF SEQ ID NOS: 4

<210> SEQ ID NO 1
<211> LENGTH: 1685
<212> TYPE: DNA
<213> ORGANISM: Picrophilus torridus

<400> SEQUENCE: 1
catatgcttg ataataatgg tttatggtac cgtgatgctg tattttatga ggttcctgta        60
aaatcattct atgattcaaa caacgatggc ataggcgatt ttaatggcct aacaatgaag       120
cttgactatt taaaaaagct tggtgttgac gctttatggc tgctgccatt ctataaatcg       180
ccattgaagg acgacggtta tgatatatct gattactatt caatactgcc ggagtatgga       240
acaattgatg attttaaaaa cttcatagat accgcgcatt caatgaacat aagggttata       300
gcggacctcg ttctaaacca tgtatctgac cagcatccat ggttcattga atcaagaagc       360
agcattgata atccaaagag ggactggttt atatggagcg acacaccaga aaaatttaag       420
```

```
gaggcaagga taatatttat agatacagaa aaatcaaact ggacctatga tccggaaaca    480
aaacagtatt actttcacag gttttactca tcccagccgg atcttaacta tgacaatcct    540
gatgtcagga acgaggttaa aaaggttata aggtactggc ttgaccttgg tcttgacggc    600
ttcagggcag atgcggttcc atacctcttt aaaagggaga atacaaactg tgagaacctg    660
ccagaaacac acaacttctt taaggaaata aggaagatga tggatgaaga ttaccctgga    720
acaatacttt tagcagaggc aaaccagtgg cctacagaaa caaaggcata ctttggtaac    780
ggcgatgaat tcacatggc attcaatttt cctttgatgc caaggatctt tatagcactg    840
gccaggagcg attactatcc aataatggat ataataaagc agacgctgcc gatacctgat    900
aactgcgact ggtgcatctt tcttagaaac catgacgagc ttacccttga tggtcacg    960 gattcagaaa gggatatcat gtacagggag tacgcaaaga taccaaagat gcgtttaaat   1020
cttggaataa ggcgcaggct agcaccgctt gctgacaatg atatcaacac aatagaacta   1080
ttaaacgcat taatatttc actgcccggc acgccgataa tatactatgg cgacgagata   1140
ggcatgggtg ataacatata tcttggcgat agaaacggtg tgagaacgcc aatgcagtgg   1200
agctatgata gaaacgcagg tttctcaatg cagattcgg agcagctcta ctcaccggtg   1260
ataacaaatc ctaattatca ttatgaaagc gtgaacgttg aggctgagct caggctgagc   1320
tcatcgcttt taaactggat gataaagatt atacatgtta gaaaggatta caaggagctc   1380
ctcggccgcg gttcaataaa atttatagag cagggtaata aaagggtgct ttcttatata   1440
agagagtatg aaaaccagag gatgctgtgc cttttttaatt tatcaaggaa tccaacgtac   1500
gttgagctaa atttaagtga ttacataggg cttaaaccaa tagaggccat aacaaaggca   1560
gcatttccaa ggataaagga tgataggtat ttcataacaa tgacaccaag gtcattcttc   1620
tggtttaatt taattgtacc tgaaagggat gattcatacg acctcattgg agaagatgcg   1680
aattc                                                              1685

<210> SEQ ID NO 2
<211> LENGTH: 1734
<212> TYPE: DNA
<213> ORGANISM: Picrophilus torridus

<400> SEQUENCE: 2
atgcttgata taatggttt atggtaccgt gatgctgtat tttatgaggt tcctgtaaaa     60
tcattctatg attcaaacaa cgatggcata ggcgatttta atggcctaac aatgaagctt    120
gactatttaa aaaagcttgg tgttgacgct ttatggctgc tgccattcta taaatcgcca    180
ttgaaggacg acggttatga tatatctgat tactattcaa tactgccgga gtatggaaca    240
attgatgatt ttaaaaactt catagatacc gcgcattcaa tgaacataag ggttatagcg    300
gacctcgttc taaaccatgt atctgaccag catccatggt tcattgaatc aagaagcagc    360
attgataatc aaagaggga ctggtttata tggagcgaca caccagaaaa atttaaggag    420
gcaaggataa tatttataga tacagaaaaa tcaaactgga cctatgatcc ggaaacaaaa    480
cagtattact ttcacaggtt ttactcatcc cagccggatc ttaactatga caatcctgat    540
gtcaggaacg aggttaaaaa ggttataagg tactggcttg accttggtct tgacggcttc    600
agggcagatg cggttccata cctctttaaa agggagaata caaactgtga gaacctgcca    660
gaaacacaca acttctttaa ggaataagg aagatgatgg atgaagatta ccctggaaca    720 atactttta g cagaggcaaa ccagtggcct acagaaacaa ggcatactt tggtaacggc    780 gatgaattc acatggcatt caattttcct ttgatgccaa ggatctttat agcactggcc    840
```

-continued

```
aggagcgatt actatccaat aatggatata ataaagcaga cgctgccgat acctgataac      900
tgcgactggt gcatctttct tagaaaccat gacgagctta cccttgagat ggtcacggat      960
tcagaaaggg atatcatgta cagggagtac gcaaagatac caaagatgcg tttaaatctt     1020
ggaataaggc gcaggctagc accgcttgct gacaatgata tcaacacaat agaactatta     1080
aacgcattaa tattttcact gcccggcacg ccgataatat actatggcga cgagataggc     1140
atgggtgata acatatatct tggcgataga aacggtgtga aacgccaat gcagtggagc     1200
tatgatagaa acgcaggttt ctcaatggca gattcggagc agctctactc accggtgata     1260
acaaatccta attatcatta tgaaagcgtg aacgttgagg ctgagctcag gctgagctca     1320
tcgcttttaa actggatgat aaagattata catgttagaa aggattacaa ggagctcctc     1380
ggccgcggtt caataaaatt tatagagcag ggtaataaaa gggtgctttc ttatataaga     1440
gagtatgaaa accagaggat gctgtgcctt tttaatttat caaggaatcc aacgtacgtt     1500
gagctaaatt taagtgatta catagggctt aaaccaatag aggccataac aaaggcagca     1560
tttccaagga taaggatga taggtatttc ataacaatga caccaaggtc attcttctgg     1620
tttaatttaa ttgtacctga aagggatgat tcatacgacc tcattggaga agatgcgaat     1680
tcccgggtcg acaagcttgc ggccgcactc gagcaccacc accaccacca ctga            1734
```

<210> SEQ ID NO 3
<211> LENGTH: 558
<212> TYPE: PRT
<213> ORGANISM: Picrophilus torridus

<400> SEQUENCE: 3

```
Met Leu Asp Asn Asn Gly Leu Trp Tyr Arg Asp Ala Val Phe Tyr Glu
1               5                   10                  15

Val Pro Val Lys Ser Phe Tyr Asp Ser Asn Asn Asp Gly Ile Gly Asp
                20                  25                  30

Phe Asn Gly Leu Thr Met Lys Leu Asp Tyr Leu Lys Lys Leu Gly Val
            35                  40                  45

Asp Ala Leu Trp Leu Leu Pro Phe Tyr Lys Ser Pro Leu Lys Asp Asp
        50                  55                  60

Gly Tyr Asp Ile Ser Asp Tyr Tyr Ser Ile Leu Pro Glu Tyr Gly Thr
65                  70                  75                  80

Ile Asp Asp Phe Lys Asn Phe Ile Asp Thr Ala His Ser Met Asn Ile
                85                  90                  95

Arg Val Ile Ala Asp Leu Val Leu Asn His Val Ser Asp Gln His Pro
            100                 105                 110

Trp Phe Ile Glu Ser Arg Ser Ser Ile Asp Asn Pro Lys Arg Asp Trp
        115                 120                 125

Phe Ile Trp Ser Asp Thr Pro Glu Lys Phe Lys Glu Ala Arg Ile Ile
    130                 135                 140

Phe Ile Asp Thr Glu Lys Ser Asn Trp Thr Tyr Asp Pro Glu Thr Lys
145                 150                 155                 160

Gln Tyr Tyr Phe His Arg Phe Tyr Ser Ser Gln Pro Asp Leu Asn Tyr
                165                 170                 175

Asp Asn Pro Asp Val Arg Asn Glu Val Lys Lys Val Ile Arg Tyr Trp
            180                 185                 190

Leu Asp Leu Gly Leu Asp Gly Phe Arg Ala Asp Ala Val Pro Tyr Leu
        195                 200                 205

Phe Lys Arg Glu Asn Thr Asn Cys Glu Asn Leu Pro Glu Thr His Asn
    210                 215                 220
```

```
Phe Phe Lys Glu Ile Arg Lys Met Met Asp Glu Asp Tyr Pro Gly Thr
225                 230                 235                 240

Ile Leu Leu Ala Glu Ala Asn Gln Trp Pro Thr Glu Thr Lys Ala Tyr
                245                 250                 255

Phe Gly Asn Gly Asp Glu Phe His Met Ala Phe Asn Phe Pro Leu Met
            260                 265                 270

Pro Arg Ile Phe Ile Ala Leu Ala Arg Ser Asp Tyr Tyr Pro Ile Met
        275                 280                 285

Asp Ile Ile Lys Gln Thr Leu Pro Ile Pro Asn Cys Asp Trp Cys
290                 295                 300

Ile Phe Leu Arg Asn His Asp Glu Leu Thr Leu Glu Met Val Thr Asp
305                 310                 315                 320

Ser Glu Arg Asp Ile Met Tyr Arg Glu Tyr Ala Lys Ile Pro Lys Met
                325                 330                 335

Arg Leu Asn Leu Gly Ile Arg Arg Leu Ala Pro Leu Ala Asp Asn
            340                 345                 350

Asp Ile Asn Thr Ile Glu Leu Leu Asn Ala Leu Ile Phe Ser Leu Pro
        355                 360                 365

Gly Thr Pro Ile Ile Tyr Tyr Gly Asp Glu Ile Gly Met Gly Asp Asn
370                 375                 380

Ile Tyr Leu Gly Asp Arg Asn Gly Val Arg Thr Pro Met Gln Trp Ser
385                 390                 395                 400

Tyr Asp Arg Asn Ala Gly Phe Ser Met Ala Asp Ser Glu Gln Leu Tyr
                405                 410                 415

Ser Pro Val Ile Thr Asn Pro Asn Tyr His Tyr Glu Ser Val Asn Val
            420                 425                 430

Glu Ala Glu Leu Arg Leu Ser Ser Ser Leu Leu Asn Trp Met Ile Lys
        435                 440                 445

Ile Ile His Val Arg Lys Asp Tyr Lys Glu Leu Leu Gly Arg Gly Ser
450                 455                 460

Ile Lys Phe Ile Glu Gln Gly Asn Lys Arg Val Leu Ser Tyr Ile Arg
465                 470                 475                 480

Glu Tyr Glu Asn Gln Arg Met Leu Cys Leu Phe Asn Leu Ser Arg Asn
                485                 490                 495

Pro Thr Tyr Val Glu Leu Asn Leu Ser Asp Tyr Ile Gly Leu Lys Pro
            500                 505                 510

Ile Glu Ala Ile Thr Lys Ala Ala Phe Pro Arg Ile Lys Asp Asp Arg
        515                 520                 525

Tyr Phe Ile Thr Met Thr Pro Arg Ser Phe Phe Trp Phe Asn Leu Ile
530                 535                 540

Val Pro Glu Arg Asp Asp Ser Tyr Asp Leu Ile Gly Glu Asp
545                 550                 555

<210> SEQ ID NO 4
<211> LENGTH: 577
<212> TYPE: PRT
<213> ORGANISM: Picrophilus torridus

<400> SEQUENCE: 4

Met Leu Asp Asn Asn Gly Leu Trp Tyr Arg Asp Ala Val Phe Tyr Glu
1               5                   10                  15

Val Pro Val Lys Ser Phe Tyr Asp Ser Asn Asn Asp Gly Ile Gly Asp
                20                  25                  30

Phe Asn Gly Leu Thr Met Lys Leu Asp Tyr Leu Lys Lys Leu Gly Val
            35                  40                  45
```

```
Asp Ala Leu Trp Leu Leu Pro Phe Tyr Lys Ser Pro Leu Lys Asp Asp
     50                  55                  60

Gly Tyr Asp Ile Ser Asp Tyr Ser Ile Leu Pro Glu Tyr Gly Thr
 65                  70                  75                  80

Ile Asp Asp Phe Lys Asn Phe Ile Asp Thr Ala His Ser Met Asn Ile
                 85                  90                  95

Arg Val Ile Ala Asp Leu Val Leu Asn His Val Ser Asp Gln His Pro
                100                 105                 110

Trp Phe Ile Glu Ser Arg Ser Ser Ile Asp Asn Pro Lys Arg Asp Trp
                115                 120                 125

Phe Ile Trp Ser Asp Thr Pro Glu Lys Phe Lys Glu Ala Arg Ile Ile
    130                 135                 140

Phe Ile Asp Thr Glu Lys Ser Asn Trp Thr Tyr Asp Pro Glu Thr Lys
145                 150                 155                 160

Gln Tyr Tyr Phe His Arg Phe Tyr Ser Ser Gln Pro Asp Leu Asn Tyr
                165                 170                 175

Asp Asn Pro Asp Val Arg Asn Glu Val Lys Lys Val Ile Arg Tyr Trp
            180                 185                 190

Leu Asp Leu Gly Leu Asp Gly Phe Arg Ala Asp Ala Val Pro Tyr Leu
        195                 200                 205

Phe Lys Arg Glu Asn Thr Asn Cys Glu Asn Leu Pro Glu Thr His Asn
    210                 215                 220

Phe Phe Lys Glu Ile Arg Lys Met Met Asp Glu Asp Tyr Pro Gly Thr
225                 230                 235                 240

Ile Leu Leu Ala Glu Ala Asn Gln Trp Pro Thr Glu Thr Lys Ala Tyr
                245                 250                 255

Phe Gly Asn Gly Asp Glu Phe His Met Ala Phe Asn Phe Pro Leu Met
            260                 265                 270

Pro Arg Ile Phe Ile Ala Leu Ala Arg Ser Asp Tyr Tyr Pro Ile Met
        275                 280                 285

Asp Ile Ile Lys Gln Thr Leu Pro Ile Pro Asn Cys Asp Trp Cys
    290                 295                 300

Ile Phe Leu Arg Asn His Asp Glu Leu Thr Leu Glu Met Val Thr Asp
305                 310                 315                 320

Ser Glu Arg Asp Ile Met Tyr Arg Glu Tyr Ala Lys Ile Pro Lys Met
                325                 330                 335

Arg Leu Asn Leu Gly Ile Arg Arg Leu Ala Pro Leu Ala Asp Asn
            340                 345                 350

Asp Ile Asn Thr Ile Glu Leu Leu Asn Ala Leu Ile Phe Ser Leu Pro
        355                 360                 365

Gly Thr Pro Ile Ile Tyr Tyr Gly Asp Glu Ile Gly Met Gly Asp Asn
    370                 375                 380

Ile Tyr Leu Gly Asp Arg Asn Gly Val Arg Thr Pro Met Gln Trp Ser
385                 390                 395                 400

Tyr Asp Arg Asn Ala Gly Phe Ser Met Ala Asp Ser Glu Gln Leu Tyr
                405                 410                 415

Ser Pro Val Ile Thr Asn Pro Asn Tyr His Tyr Glu Ser Val Asn Val
            420                 425                 430

Glu Ala Glu Leu Arg Leu Ser Ser Ser Leu Leu Asn Trp Met Ile Lys
        435                 440                 445

Ile Ile His Val Arg Lys Asp Tyr Lys Glu Leu Leu Gly Arg Gly Ser
    450                 455                 460

Ile Lys Phe Ile Glu Gln Gly Asn Lys Arg Val Leu Ser Tyr Ile Arg
```

-continued

```
                 465                 470                 475                 480
        Glu Tyr Glu Asn Gln Arg Met Leu Cys Leu Phe Asn Leu Ser Arg Asn
                        485                 490                 495

Pro Thr Tyr Val Glu Leu Asn Leu Ser Asp Tyr Ile Gly Leu Lys Pro
                    500                 505                 510

Ile Glu Ala Ile Thr Lys Ala Ala Phe Pro Arg Ile Lys Asp Asp Arg
                515                 520                 525

Tyr Phe Ile Thr Met Thr Pro Arg Ser Phe Phe Trp Phe Asn Leu Ile
                530                 535                 540

Val Pro Glu Arg Asp Asp Ser Tyr Asp Leu Ile Gly Glu Asp Ala Asn
        545                 550                 555                 560

Ser Arg Val Asp Lys Leu Ala Ala Ala Leu Glu His His His His His
                        565                 570                 575

His
```

COMPOSITION CONTAINING TREHALOSE SYNTHASE AND METHODS OF USE THEREOF

FIELD OF THE INVENTION

The present invention relates to the isolation and functional identification of a novel acid and heat resistant trehalose synthase enzyme cloned from *Picrophilus torridus*. More particularly, the present invention discloses the DNA sequence for the *Picrophilus torridus* trehalose synthase gene, PTTS, which when expressed in a heterologous host such as *Escherichia coli*, provides enzymatic activity that catalyzes the direct interconversion of maltose and trehalose through intramolecular transglycosylation. Additionally, the present invention teaches methods of use of PTTS for production of trehalose as well as for production of various useful compounds comprising trehalose.

BACKGROUND OF THE INVENTION

Trehalose [α-D-glucopyranosyl α-D-glucopyranoside] is a naturally occurring nonreducing disaccharide in which the two glucose molecules are linked through an 1,1-glycosidic bond. Though three anomers of trehalose exist, which are α,α-1,1-, α,β-1,1,- and β,β-1,1-trehalose, only the α,α-1,1-form is widespread in nature and present in a large number of organisms, including bacteria, yeast, fungi, insects, invertebrates, and plants (1). The function of trehalose in organisms varies. In addition to serving as an energy and carbon source, trehalose is the basic component of various cell wall glycolipids of mycobacteria and corynebacteria, which adds to the impermeability of the cell walls and has been implicated in the pathogenesis of diseases caused by such bacteria (2, 3).

In yeast and plants, trehalose or a related metabolite, trehalose-6-phosphate, acts as a signaling or regulatory molecule that interferes with pathways associated with energy metabolism or even affects growth and development (4-6). Moreover, trehalose has been found to help organisms acquire tolerance to various stresses, including cold, heat, desiccation, dehydration, and osmotic and oxidative stress (1, 7-10). This quality is attributed to its "chemical chaperon" property, namely its ability to maintain proteins and membranes in their native conformations (1, 8, 11), or to its presumed ability to quench the oxygen radical (10).

Three main pathways specifying the biosynthesis of trehalose have been identified in various organisms (12). The first pathway utilizes trehalose-phosphate (P) synthase (EC 2.4.1.15) (OtsA in *Escherichia coli*) that catalyzes the transfer of glucose from UDP-glucose to glucose-6-P to form trehalose-P and UDP. The phosphate is then removed by trehalose-P phosphatase (EC 3.1.3.12) (OtsB in *E. coli*) to give free trehalose (13).

The second pathway also involves two enzymes called maltooligosyl trehalose synthase (EC 5.4.99.15) and maltooligosyl trehalose trehalohydrolase (EC 3.2.1.141). The former enzyme first converts the α1,4-linkage in the reducing end of the maltooligosaccharide chain into the α1,1-linkage and then the latter enzyme hydrolyzes the reducing-end disaccharide to release one molecule of trehalose (14-16).

The third pathway, catalyzed by trehalose synthase (TSase) (EC 5.4.99.16), involves the direct conversion of maltose into trehalose by an intramolecular rearrangement of the α-1,4-linkage of maltose to the α-1,1-linkage of trehalose (17). Since this pathway allows one-step formation of trehalose and an inexpensive substrate, maltose, is employed, it is highly useful for the industrial manufacture of trehalose.

At this time, approximately six different trehalose synthases have been reported from different species and characterized for their biochemical properties (18-23). However, the trehalose synthases of the prior art are characterized by biochemical properties, including their low tolerance for heat and acidity, that may be undesirable in certain applications or in use in certain environments. For example, the three trehalose synthases from *Pimelobacter* sp. R48, *Thermobifida fusca*, and *Pseudomonas stutzeri* CJ38 are thermolabile. Although the trehalose synthase from *Thermus aquaticus* on the contrary is highly thermostable, this enzyme has the drawback of low enzyme yield in the original organism, which is undesirable for industrial scale preparation of the enzyme because a culture of a large volume of organisms is required for enzyme isolation. In addition, the trehalose synthase enzymes are most active at a pH that is near or above neutral, which precludes these enzymes from being useful in even slightly acidic environments. Therefore, there is a current need in the art for a trehalose synthase enzyme which retains high degree of activity at higher temperatures and in more acidic environments than the trehalose synthases of the prior art.

The present invention teaches the biochemical properties of a novel recombinant trehalose synthase from *Picrophilus torridus*, a hyperacidophilic, thermophilic, heterotrophic and absolutely aerobic archaea, which grows optimally at 60° C. and pH 0.7 (13). The novel *Picrophilus torridus* trehalose synthase of the present invention has superior heat resistant and acid resistant qualities when compared to trehalose synthases of the prior art. The heat resistant and acid resistant trehalose synthase of the present invention offers a significant advantage for industrial production of trehalose by increasing the solubility of substrate and reducing the risk of contamination during production.

SUMMARY OF THE INVENTION

Trehalose synthase enzyme catalyzes the one-step production of trehalose from maltose via an intramolecular transglycosylation. Unlike the previously known trehalose synthase enzymes, the trehalose synthase of the present invention retains high activity and stability under high temperature and acidic conditions. Due to its acid and heat resistant properties, the *Picrophilus torridus* trehalose synthase of the present invention provides a valuable route for the reliable and cost effective production of trehalose from a readily available inexpensive starting material, maltose.

In one embodiment, the present invention relates to an isolated and purified nucleic acid sequence encoding a functional *Picrophilus torridus* trehalose synthase protein such that the protein has a catalytic activity of catalyzing the intramolecular rearrangement of the α1,4-linkage of maltose to the α1,1-linkage of trehalose, or vice versa.

In another embodiment, the present invention relates to an isolated and purified DNA sequence wherein the sequence is:

(SEQ ID NO: 1)

CATATGCTTGATAATAATGGTTTATGGTACCGTGATGCTGTATTTTATGAGGTTCCT

GTAAAATCATTCTATGATTCAAACAACGATGGCATAGGCGATTTTAATGGCCTAACA

ATGAAGCTTGACTATTTAAAAAAGCTTGGTGTTGACGCTTTATGGCTGCTGCCATTC

TATAAATCGCCATTGAAGGACGACGGTTATGATATATCTGATTACTATTCAATACTG

CCGGAGTATGGAACAATTGATGATTTTAAAAACTTCATAGATACCGCGCATTCAATG

AACATAAGGGTTATAGCGGACCTCGTTCTAAACCATGTATCTGACCAGCATCCATG

GTTCATTGAATCAAGAAGCAGCATTGATAATCCAAAGAGGGACTGGTTTATATGGA

GCGACACACCAGAAAAATTTAAGGAGGCAAGGATAATATTTATAGATACAGAAAAA

TCAAACTGGACCTATGATCCGGAAACAAAACAGTATTACTTTCACAGGTTTTACTCA

TCCCAGCCGGATCTTAACTATGACAATCCTGATGTCAGGAACGAGGTTAAAAAGGT

TATAAGGTACTGGCTTGACCTTGGTCTTGACGGCTTCAGGGCAGATGCGGTTCCAT

ACCTCTTTAAAAGGGAGAATACAAACTGTGAGAACCTGCCAGAAACACACAACTTC

TTTAAGGAAATAAGGAAGATGATGGATGAAGATTACCCTGGAACAATACTTTTAGCA

GAGGCAAACCAGTGGCCTACAGAAACAAAGGCATACTTTGGTAACGGCGATGAAT

TTCACATGGCATTCAATTTTCCTTTGATGCCAAGGATCTTTATAGCACTGGCCAGGA

GCGATTACTATCCAATAATGGATATAATAAAGCAGACGCTGCCGATACCTGATAAC

TGCGACTGGTGCATCTTTCTTAGAAACCATGACGAGCTTACCCTTGAGATGGTCAC

GGATTCAGAAAGGGATATCATGTACAGGGAGTACGCAAAGATACCAAAGATGCGTT

TAAATCTTGGAATAAGGCGCAGGCTAGCACCGCTTGCTGACAATGATATCAACACA

ATAGAACTATTAAACGCATTAATATTTTCACTGCCCGGCACGCCGATAATATACTAT

GGCGACGAGATAGGCATGGGTGATAACATATATCTTGGCGATAGAAACGGTGTGA

GAACGCCAATGCAGTGGAGCTATGATAGAAACGCAGGTTTCTCAATGGCAGATTC

GGAGCAGCTCTACTCACCGGTGATAACAAATCCTAATTATCATTATGAAAGCGTGA

ACGTTGAGGCTGAGCTCAGGCTGAGCTCATCGCTTTTAAACTGGATGATAAAGATT

ATACATGTTAGAAAGGATTACAAGGAGCTCCTCGGCCGCGGTTCAATAAAATTTAT

AGAGCAGGGTAATAAAAGGGTGCTTTCTTATATAAGAGAGTATGAAAACCAGAGGA

TGCTGTGCCTTTTTAATTTATCAAGGAATCCAACGTACGTTGAGCTAAATTTAAGTG

ATTACATAGGGCTTAAACCAATAGAGGCCATAACAAAGGCAGCATTTCCAAGGATA

AAGGATGATAGGTATTTCATAACAATGACACCAAGGTCATTCTTCTGGTTTAATTTA

ATTGTACCTGAAAGGGATGATTCATACGACCTCATTGGAGAAGAT░░GAATTC.

In another embodiment, the present invention relates to an isolated and purified DNA sequence wherein the sequence is:

(SEQ ID NO: 2)
<u>ATG</u>CTTGATAATAATGGTTTATGGTACCGTGATGCTGTATTTTATGAGGT

TCCTGTAAAATCATTCTATGATTCAAACAACGATGGCATAGGCGATTTTA

ATGGCCTAACAATGAAGCTTGACTATTTAAAAAAGCTTGGTGTTGACGCT

TTATGGCTGCTGCCATTCTATAAATCGCCATTGAAGGACGACGGTTATGA

TATATCTGATTACTATTCAATACTGCCGGAGTATGGAACAATTGATGATT

TTAAAAACTTCATAGATACCGCGCATTCAATGAACATAAGGGTTATAGCG

GACCTCGTTCTAAACCATGTATCTGACCAGCATCCATGGTTCATTGAATC

AAGAAGCAGCATTGATAATCCAAAGAGGGACTGGTTTATATGGAGCGACA

CACCAGAAAAATTTAAGGAGGCAAGGATAATATTTATAGATACAGAAAAA

TCAAACTGGACCTATGATCCGGAAACAAAACAGTATTACTTTCACAGGTT

TTACTCATCCCAGCCGGATCTTAACTATGACAATCCTGATGTCAGGAACG

AGGTTAAAAAGGTTATAAGGTACTGGCTTGACCTTGGTCTTGACGGCTTC

AGGGCAGATGCGGTTCCATACCTCTTTAAAAGGGAGAATACAAACTGTGA

GAACCTGCCAGAAACACACAACTTCTTTAAGGAAATAAGGAAGATGATGG

ATGAAGATTACCCTGGAACAATACTTTTAGCAGAGGCAAACCAGTGGCCT

ACAGAAACAAAGGCATACTTTGGTAACGGCGATGAATTTCACATGGCATT

CAATTTTCCTTTGATGCCAAGGATCTTTATAGCACTGGCCAGGAGCGATT

ACTATCCAATAATGGATATAATAAAGCAGACGCTGCCGATACCTGATAAC

-continued

```
TGCGACTGGTGCATCTTTCTTAGAAACCATGACGAGCTTACCCTTGAGAT
GGTCACGGATTCAGAAAGGGATATCATGTACAGGGAGTACGCAAAGATAC
CAAAGATGCGTTTAAATCTTGGAATAAGGCGCAGGCTAGCACCGCTTGCT
GACAATGATATCAACACAATAGAACTATTAAACGCATTAATATTTTCACT
GCCCGGCACGCCGATAATATACTATGGCGACGAGATAGGCATGGGTGATA
ACATATATCTTGGCGATAGAAACGGTGTGAGAACGCCAATGCAGTGGAGC
TATGATAGAAACGCAGGTTTCTCAATGGCAGATTCGGAGCAGCTCTACTC
ACCGGTGATAACAAATCCTAATTATCATTATGAAAGCGTGAACGTTGAGG
CTGAGCTCAGGCTGAGCTCATCGCTTTTAAACTGGATGATAAAGATTATA
CATGTTAGAAAGGATTACAAGGAGCTCCTCGGCCGCGGTTCAATAAAATT
TATAGAGCAGGGTAATAAAAGGGTGCTTTCTTATATAAGAGAGTATGAAA
ACCAGAGGATGCTGTGCCTTTTTAATTTATCAAGGAATCCAACGTACGTT
GAGCTAAATTTAAGTGATTACATAGGGCTTAAACCAATAGAGGCCATAAC
AAAGGCAGCATTTCCAAGGATAAAGGATGATAGGTATTTCATAACAATGA
CACCAAGGTCATTCTTCTGGTTTAATTTAATTGTACCTGAAAGGGATGAT
TCATACGACCTCATTGGAGAAGATGCGAATTCCCGGGTCGACAAGCTTGC
GGCCGCACTCGAGCACCACCACCACCACCACTGA.
```

In yet another embodiment, the present invention relates to an isolated and purified DNA sequence wherein the sequence encodes a protein of the sequence:

(SEQ ID NO: 3)
MLDNNGLWYRDAVFYEVPVKSFYDSNNDGIGDFNGLTMKLDYLKKLGVDA

LWLLPFYKSPLKDDGYDISDYYSILPEYGTIDDFKNFIDTAHSMNIRVIA

DLVLNHVSDQHPWFIESRSSIDNPKRDWFIWSDTPEKFKEARIIFIDTEK

SNWTYDPETKQYYFHRFYSSQPDLNYDNPDVRNEVKKVIRYWLDLGLDGF

RADAVPYLFKRENTNCENLPETHNFFKEIRKMMDEDYPGTILLAEANQWP

TETKAYFGNGDEFHMAFNFPLMPRIFIALARSDYYPIMDIIKQTLPIPDN

CDWCIFLRNHDELTLEMVTDSERDIMYREYAKIPKMRLNLGIRRRLAPLA

DNDINTIELLNALIFSLPGTPIIYYGDEIGMGDNIYLGDRNGVRTPMQWS

YDRNAGFSMADSEQLYSPVITNPNYHYESVNVEAELRLSSSLLNWMIKII

HVRKDYKELLGRGSIKFIEQGNKRVLSYIREYENQRMLCLFNLSRNPTYV

ELNLSDYIGLKPIEAITKAAFPRIKDDRYFITMTPRSFFWFNLIVPERDD

SYDLIGED.

In yet another embodiment, the present invention relates to an isolated and purified DNA sequence wherein the sequence encodes a protein of the sequence:

(SEQ ID NO: 4)
MLDNNGLWYRDAVFYEVPVKSFYDSNNDGIGDFNGLTMKLDYLKKLGVDALWLLPFY

KSPLKDDGYDISDYYSILPEYGTIDDFKNFIDTAHSMNIRVIADLVLNHVSDQHPWFIESR

SSIDNPKRDWFIWSDTPEKFKEARIIFIDTEKSNWTYDPETKQYYFHRFYSSQPDLNYD

NPDVRNEVKKVIRYWLDLGLDGFRADAVPYLFKRENTNCENLPETHNFFKEIRKMMDE

DYPGTILLAEANQWPTETKAYFGNGDEFHMAFNFPLMPRIFIALARSDYYPIMDIIKQTL

PIPDNCDWCIFLRNHDELTLEMVTDSERDIMYREYAKIPKMRLNLGIRRRLAPLADNDIN

LYSPVITNPNYHYESVNVEAELRLSSSLLNWMIKIIHVRKDYKELLGRGSIKFIEQGNKR

VLSYIREYENQRMLCLFNLSRNPTYVELNLSDYIGLKPIEAITKAAFPRIKDDRYFITMTP

RSFFWFNLIVPERDDSYDLIGEDANSRVDKLAAALEHHHHHH.

In another embodiment, the present invention relates to an isolated and purified nucleic acid sequence encoding a functional *Picrophilus torridus* trehalose synthase protein, wherein the sequence is a nucleic acid sequence that is at least 95% identical to SEQ ID NO: 1 or SEQ ID NO: 2, provided that the nucleic acid sequence is translated into a protein encoding a functional *Picrophilus torridus* trehalose synthase protein such that the protein has a catalytic activity of catalyzing the intramolecular rearrangement of the α1,4-linkage of maltose to the α1,1-linkage of trehalose, or vice versa. Greater degrees of identity to these sequences, such as 97.5% identity or 99% identity, are also within the scope of the invention.

In another embodiment, the present invention relates to an isolated and purified DNA sequence encoding a functional *Picrophilus torridus* trehalose synthase protein, wherein the DNA sequence is selected from the group consisting of:
(a) SEQ ID NO: 1; and
(b) a DNA sequence encoding a protein differing by from one to 20 conservative amino acid substitutions from SEQ ID NO: 3, wherein the protein encoded is a functional *Picrophilus torridus* trehalose synthase protein such that the protein has a catalytic activity of catalyzing the intramolecular rearrangement of the α1,4-linkage of maltose to the α1,1-linkage of trehalose, or vice versa, and wherein a conservative amino acid substitution is one of the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. DNA sequences encoding proteins with fewer conservative amino acid substitutions, such as from one to 10 conservative amino acid substitutions, one to five conservative amino acid substitutions, or one to two conservative amino acid substitutions, are also within the scope of the invention.

In another embodiment, the present invention relates to an isolated and purified DNA sequence encoding a functional *Picrophilus torridus* trehalose synthase protein, wherein the DNA sequence is selected from the group consisting of:

(a) SEQ ID NO: 2; and (b) a DNA sequence encoding a protein differing by from one to 20 conservative amino acid substitutions from SEQ ID NO: 4, wherein the protein encoded is a functional *Picrophilus torridus* trehalose synthase protein such that the protein has a catalytic activity of catalyzing the intramolecular rearrangement of the α1,4-linkage of maltose to the α1,1-linkage of trehalose, or vice versa, and wherein a conservative amino acid substitution is one of the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. DNA sequences encoding proteins with fewer conservative amino acid substitutions, such as from one to 10 conservative amino acid substitutions, one to five conservative amino acid substitutions, or one to two conservative amino acid substitutions, are also within the scope of the invention.

In yet another embodiment, the present invention relates to a vector comprising an isolated and purified DNA sequence encoding a functional *Picrophilus torridus* trehalose synthase protein such that the protein has a catalytic activity of successfully catalyzing the intramolecular rearrangement of the α1,4-linkage of maltose to the α1,1-linkage of trehalose, or vice versa. The DNA sequences include those described above.

In another embodiment, the present invention relates to a host cell transformed or transfected with a vector comprising an isolated and purified DNA sequence encoding a functional *Picrophilus torridus* trehalose synthase protein such that the protein has a catalytic activity of catalyzing the intramolecular rearrangement of the α1,4-linkage of maltose to the α1,1-linkage of trehalose, or vice versa. The vectors and isolated and purified DNA sequences are as described above.

In another embodiment, the present invention relates to a method of producing an isolated protein having *Picrophilus torridus* trehalose synthase protein activity such that the protein has a catalytic activity of catalyzing the intramolecular rearrangement of the α1,4-linkage of maltose to the α1,1-linkage of trehalose, or vice versa, comprising the steps of:

(a) culturing a host cell according to the present invention as described above under conditions wherein a protein having *Picrophilus torridus* trehalose synthase activity is expressed by the host cell; and (b) isolating the protein having *Picrophilus torridus* trehalose synthase activity so that isolated protein is produced.

In another embodiment, the present invention relates to an isolated and purified protein molecule having functional *Picrophilus torridus* trehalose synthase activity such that the protein has a catalytic activity of catalyzing the intramolecular rearrangement of the α1,4-linkage of maltose to the α1,1-linkage of trehalose, or vice versa. The isolated and purified protein molecule can have the amino acid sequence of SEQ ID NO: 3 or SEQ ID NO: 4, or can be another isolated and purified protein molecule according to the present invention as described above, including a protein molecule produced by the translation of isolated and purified DNA sequences according to the present invention as described above. The isolated and purified protein molecule can be a mutein or variant of SEQ ID NO: 3 or SEQ ID NO: 4 including one to 20 conservative amino acid substitutions as described above.

In another embodiment, the present invention relates to a method of producing trehalose comprising the step of reacting the isolated and purified protein molecule having functional *Picrophilus torridus* trehalose synthase activity with maltose under conditions in which the protein molecule catalyzes the intramolecular rearrangement of the α1,4-linkage of maltose to the α1,1-linkage of trehalose. The isolated and purified protein molecule is one of those described above as within the scope of the invention.

In yet another embodiment, the present invention relates to a method for producing a mutein of *Picrophilus torridus* trehalose synthase with at least one altered property selected from the group consisting of regiospecificity and stereospecificity comprising the steps of:

(1) threading the wild-type *Picrophilus torridus* trehalose synthase amino acid sequence onto the three-dimensional structure of a mammalian analogue enzyme;

(2) docking at least one maltose substrate into the predicted active site pocket;

(3) mapping amino acid residues within a defined distance of the modeled substrate molecules and rationalizing the amino acid residues with predicted chemical transformations catalyzed by the *Picrophilus torridus* trehalose synthase to identify amino acid residues capable of steric, ionic, electronic and hydrophobic interactions with the substrate molecules;

(4) selecting at least one altered amino acid residue for its potential for substrate binding and positioning of the substrate molecule relative to the heme-catalytic center; and (5) introducing the at least one altered amino acid amino acid residue by site-directed mutagenesis to produce the mutein.

BRIEF DESCRIPTION OF THE DRAWINGS

The following invention will become better understood with reference to the specification, appended claims, and accompanying drawings, where:

FIG. 6 illustrates the alignment of amino acid sequences of trehalose synthases from *Picrophilus torridus* trehalose synthase (PTTS), *Pimelobacter* sp. R48 (PSTS) and *T. aquaticus* (TATS), oligo-1,6-glucosidases from *Bacillus subtilis* (BSOG) and *B. cereus* (BCOG), and isomaltulose synthase from *Klebsiella* sp. LX3 (PaII). The conserved active sites and substrate-binding sites were denoted by asterisks. Protein sequence alignment was performed using Vector NTI suite 7.0 (Informax Inc., Bethesda, Md., USA).

FIG. 7 is a table demonstrating the kinetic parameters of *Picrophilus torridus* trehalose synthase enzyme for various substrates. $K_m$, $V_{max}$, $k_{cat}$, and $k_{cat}/K_m$ are shown.

FIG. 8 is a table demonstrating the effects of metal ions and reagents on the enzymatic activity of *Picrophilus torridus* trehalose synthase.

FIG. 9 is a table comparing the relative specific activity of wild type *Picrophilus torridus* trehalose synthase and its mutant enzymes. The percentage relative activities are represented as the ratio of mutants to wild type.

DETAILED DESCRIPTION OF THE INVENTION

Abbreviations and Terms

Figure 1:
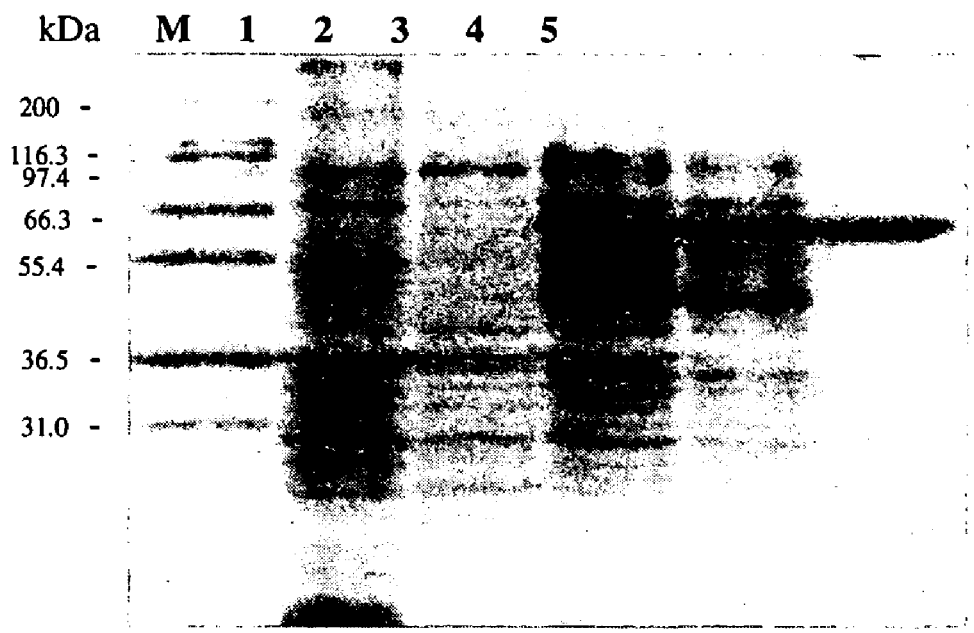
FIG. 1 illustrates the results of the 12% SDS-PAGE analysis for the purification of recombinant *Picrophilus torridus* trehalose synthase. Lanes 1 and 2 were total cell lysate and soluble fraction, respectively, obtained from a non-expression control of Rosetta-gami B transformed with pET-23a(+)-PTTS plasmid. Lanes 3 and 4 were total cell lysate and soluble fraction, respectively, obtained from Rosetta-gami B(DE3) transformed with pET-23a(+)-PTTS. Lane 5 was the purified recombinant PTTS after Ni-column purification. Lane M was protein molecular weight marker indicated in kDa.

In accordance with the present invention and as used herein, the following terms and abbreviations are defined with the following meanings, unless explicitly stated otherwise. These explanations are intended to be exemplary only. They are not intended to limit the terms as they are described or referred to throughout the specification. Rather, these explanations are meant to include any additional aspects and/or examples of the terms as described and claimed herein.

The following abbreviations are used herein:

The term "PTTS" refers to the *Picrophilus torridus* trehalose synthase enzyme of the present invention.

The phrase "substantially identical" means that a relevant sequence is at least 70%, 75%, 80%, 85%, 90%, 92%, 95%, 96%, 97%, 98%, or 99% identical to a given sequence. By way of example, such sequences may be allelic variants, sequences derived from various species, or they may be derived from the given sequence by truncation, deletion, amino acid substitution or addition. Percent identity between two sequences is determined by standard alignment algorithms such as ClustalX when the two sequences are in best alignment according to the alignment algorithm.

As used herein, the term "hybridization" or "hybridizes" under certain conditions is intended to describe conditions for hybridization and washes under which nucleotide sequences that are significantly identical or homologous to each other remain bound to each other. Appropriate hybridization conditions can be selected by those skilled in the art with minimal experimentation as exemplified in Ausubel, F. A., et al., eds., Current Protocols in Molecular Biology Vol. 2, John Wiley and Sons, Inc., New York (1995). Additionally, stringency conditions are described in Sambrook et al. Molecular Cloning: A Laboratory Manual, 2nd ed., Cold Spring Harbor Laboratory Press, New York (1989). Variations on the conditions for low, moderate, and high stringency are well known in the art and may be used with the current invention.

As used herein, the term "nucleic acid," "nucleic acid sequence," "polynucleotide," or similar terms, refers to a deoxyribonucleotide or ribonucleotide oligonucleotide or polynucleotide, including single- or double-stranded forms, and coding or non-coding (e.g., "antisense") forms unless otherwise specified. The term encompasses nucleic acids containing known analogues of natural nucleotides. The term also encompasses nucleic acids including modified or substituted bases as long as the modified or substituted bases interfere neither with the Watson-Crick binding of complementary nucleotides or with the binding of the nucleotide sequence by proteins that bind specifically. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described, e.g., by U.S. Pat. Nos. 6,031,092; 6,001,982; 5,684,148; see also, WO 97/03211; WO 96/39154; Mata (1997) Toxicol. Appl. Pharmacol. 144:189-197. Other synthetic backbones encompassed by the term include methylphosphonate linkages or alternating methylphosphonate and phosphodiester linkages (see, e.g., U.S. Pat. No. 5,962, 674; Strauss-Soukup (1997) Biochemistry 36:8692-8698), and benzylphosphonate linkages (see, e.g., U.S. Pat. No. 5,532,226; Samstag (1996) Antisense Nucleic Acid Drug Dev 6:153-156). The nucleotide sequence or molecule may also be referred to as a "nucleotide probe." Some of the nucleic acid molecules of the invention are derived from DNA or RNA isolated at least once in substantially pure form and in a quantity or concentration enabling identification, manipulation, and recovery of its component nucleotide sequence by standard biochemical methods. Examples of such methods, including methods for PCR protocols that may be used herein, are disclosed in Sambrook et al. Molecular Cloning: A Laboratory Manual, 2nd ed., Cold Spring Harbor Laboratory Press, New York (1989), Ausubel, F. A., et al., eds., Current Protocols in Molecular Biology, John Wiley and Sons, Inc., New York (1987), and Innis, M., et al. (Eds.) PCR Protocols: A Guide to Methods and Applications, Academic Press, San Diego, Calif. (1990). Reference to a nucleic acid molecule also includes its complement as determined by the standard Watson-Crick base-pairing rules, with uracil (U) in RNA replacing thymine (T) in DNA, unless the complement is specifically excluded.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

As described herein, the nucleic acid molecules of the invention include DNA in both single-stranded and double-stranded form, as well as the DNA or RNA complement thereof. DNA includes, for example, DNA, genomic DNA, chemically synthesized DNA, DNA amplified by PCR, and combinations thereof. Genomic DNA, including translated, non-translated and control regions, may be isolated by conventional techniques, e.g., using any one of the cDNAs of the invention, or suitable fragments thereof, as a probe, to identify a piece of genomic DNA which can then be cloned using methods commonly known in the art.

Polypeptides encoded by the nucleic acids of the invention are encompassed by the invention. As used herein, reference to a nucleic acid "encoding" a protein or polypeptide encompasses not only cDNAs and other intronless nucleic acids, but also DNAs, such as genomic DNA, with introns, on the assumption that the introns included have appropriate splice donor and acceptor sites that will ensure that the introns are spliced out of the corresponding transcript when the transcript is processed in a eukaryotic cell. Due to the degeneracy of the genetic code wherein more than one codon can encode the same amino acid, multiple DNA sequences can code for the same polypeptide. Such variant DNA sequences can result from genetic drift or artificial manipulation (e.g., occurring during PCR amplification or as the product of deliberate mutagenesis of a native sequence). Deliberate mutagenesis of a native sequence can be carried out using numerous techniques well known in the art. For example, oligonucleotide-directed site-specific mutagenesis procedures can be employed, particularly where it is desired to mutate a gene such that predetermined restriction nucleotides or codons are altered by substitution, deletion or insertion. Exemplary methods of making such alterations are disclosed by Walder et al. (Gene 42:133, 1986); Bauer et al. (Gene 37:73, 1985); Craik (BioTechniques, Jan. 12-19, 1985); Smith et al. (Genetic Engineering: Principles and Methods, Plenum Press, 1981); Kunkel (Proc. Natl. Acad. Sci. USA 82:488, 1985); Kunkel et al. (Methods in Enzymol. 154.367, 1987). The present invention thus encompasses any nucleic acid capable of encoding a protein of the current invention.

DNA sequences encoding the polypeptides or proteins of the invention can be obtained by several methods. For example, the DNA can be isolated using hybridization procedures that are well known in the art. These include, but are not limited to: (1) hybridization of probes to genomic or cDNA libraries to detect shared nucleotide sequences; (2) antibody screening of expression libraries to detect shared structural features; and (3) synthesis by the polymerase chain reaction (PCR). RNA sequences of the invention can be obtained by methods known in the art (See, for example, Current Protocols in Molecular Biology, Ausubel, et al., Eds., 1989).

The development of specific DNA sequences encoding proteins or polypeptides of the invention can be obtained by: (1) isolation of a double-stranded DNA sequence from the genomic DNA; (2) chemical manufacture of a DNA sequence to provide the necessary codons for the polypeptide of interest; and (3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA is the least common. This is especially true when it is desirable to obtain the microbial expression of eukaryotic polypeptides due to the presence of introns. For obtaining proteins or polypeptides according to the present invention, the synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells that have a high level of genetic expression. When used in combination with polymerase chain reaction technology, even rare expression products can be clones. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., Nucleic Acid Research 11:2325, 1983).

With respect to nucleotide sequences that are within the scope of the invention, all nucleotide sequences encoding the proteins or polypeptides that are embodiments of the invention as described are included in nucleotide sequences that are within the scope of the invention. This further includes all nucleotide sequences that encode polypeptides according to the invention that incorporate conservative amino acid substitutions as defined above. This further includes nucleotide sequences that encode larger proteins incorporating the proteins or polypeptides, including fusion proteins, and proteins that incorporate amino-terminal or carboxyl-terminal flanking sequences.

Nucleic acid sequences of the present invention further include nucleic acid sequences that are at least 95% identical to the sequences above, with the proviso that the nucleic acid sequences retain the activity of the sequences before substitutions of bases are made, including any activity of proteins that are encoded by the nucleotide sequences and any activity of the nucleotide sequences that is expressed at the nucleic acid level, such as the binding sites for proteins affecting transcription. Preferably, the nucleic acid sequences are at least 97.5% identical. More preferably, they are at least 99% identical. For these purposes, "identity" is defined according to the Needleman-Wunsch algorithm (S. B. Needleman & C. D. Wunsch, "A General Method Applicable to the Search for Similarities in the Amino Acid Sequence of Two Proteins," *J. Mol. Biol.* 48: 443-453 (1970)).

The current invention provides for isolated polypeptides. As used herein, the term "polypeptides" refers to a genus of polypeptide or peptide fragments that encompass the amino acid sequences identified herein, as well as smaller fragments. Alternatively, a polypeptide may be defined in terms of its antigenic relatedness to any peptide encoded by the nucleic acid sequences of the invention. Thus, in one embodiment, a polypeptide within the scope of the invention is defined as an amino acid sequence comprising a linear or 3-dimensional epitope shared with any peptide encoded by the nucleic acid sequences of the invention. Alternatively, a polypeptide within the scope of the invention is recognized by an antibody that specifically recognizes any peptide encoded by the nucleic acid sequences of the invention. Antibodies are defined to be specifically binding if they bind polypeptides of the invention with a $K_a$ of greater than or equal to about $10^7$ $M^{-1}$, such as greater than or equal to $10^8 M^{-1}$. As used herein, the term "isolated," in reference to polypeptides or proteins, means that the polypeptide or protein is substantially removed from polypeptides, proteins, nucleic acids, or other macromolecules with which it, or its analogues, occurs in nature. Although the term "isolated" is not intended to require a specific degree of purity, typically, the protein will be at least about 75% pure, more typically at least about 90% pure, preferably at least about 95% pure, and more preferably at least about 99% pure.

A polypeptide "variant" as referred to herein means a polypeptide substantially homologous to a native polypeptide, but which has an amino acid sequence different from that encoded by any of the nucleic acid sequences of the invention because of one or more deletions, insertions or substitutions. Variants can comprise conservatively substituted sequences, meaning that a given amino acid residue is replaced by a residue having similar physiochemical characteristics. See Zubay, Biochemistry, Addison-Wesley Pub. Co. (1983). In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g. Watson et al. Molecular Biology of the Gene, 4th Edition, 1987, Benjamin/Cummings, p. 224). In particular, such a conservative variant has a modified amino acid sequence, such that the change(s) do not substantially alter the protein's (the conservative variant's) structure and/or activity, e.g., antibody activity, enzymatic activity, or receptor activity. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue followed by exemplary substitution): Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. An alternative exemplary guideline uses the following six groups, each containing amino acids that are conservative substitutions for one another: (1) alanine (A or Ala), serine (S or Ser), threonine (T or Thr); (2) aspartic acid (D or Asp), glutamic acid (E or Glu); (3) asparagine (N or Asn), glutamine (Q or Gln); (4) arginine (R or Arg), lysine (K or Lys); (5) isoleucine (I or Ile), leucine (L or Leu), methionine (M or Met), valine (V or Val); and (6) phenylalanine (F or Phe), tyrosine (Y or Tyr), tryptophan (W or Trp); (see also, e.g., Creighton (1984) Proteins, W. H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations" when the three-dimensional structure and the function of the protein to be delivered are conserved by such a variation. As further exemplified below in Example 5, it is generally preferred that such conservative amino acid substitutions be made outside of the substrate recognition sequences (SRS) SRS1, SRS2, SRS3, SRS4, SRS5, or SRS6. However in some cases these conservative amino acid substitutions can be made in the substrate recognition sequences SRS1, SRS2, SRS3, SRS4, SRS5, or SRS6 if molecular modeling according to techniques known in the art indicates that such substitutions do not alter the enzyme specificity.

The effects of such substitutions can be calculated using substitution score matrices such PAM120, PAM-200, and PAM-250 as discussed in Altschul, (J. Mol. Biol. 219:55565 (1991)). Other such conservative substitutions, for example, substitutions of entire regions having similar hydrophobicity characteristics, are well known.

Naturally-occurring protein variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides encoded by the sequences of the invention.

Variants of the trehalose synthase of the present invention may be used to attain desired enhanced or reduced enzymatic activity, modified regiochemistry or stereochemistry, or altered substrate utilization or product distribution. A variant or site directed mutant may be made by any methods known in the art. Variants and derivatives of native polypeptides can be obtained by isolating naturally-occurring variants, or the nucleotide sequence of variants, of other or same plant lines or species, or by artificially programming mutations of nucleotide sequences coding for native citrus polypeptides. Methods for site-directed mutagenesis are well-known in the art and include, but are not limited to, the methods described in J. Sambrook & D. W. Russell, "Molecular Cloning: A Laboratory Manual" (3d ed., Cold Spring Harbor Laboratory Press, Cold Spring Harbor, N.Y., 2001), ch. 13, incorporated herein by this reference.

In one embodiment, the invention contemplates vectors comprising the nucleic acids of the invention. As used herein, the term "vector" refers to a plasmid, virus, phagemid, or other vehicle known in the art that has been manipulated by insertion or incorporation of heterologous DNA, such as nucleic acid encoding proteins or polypeptides according to the present invention. Vectors include, but are not limited to, expression vectors; vectors suitable for other purposes that are not expression vectors are known in the art. Such expression vectors typically contain a promoter sequence for efficient transcription of the inserted nucleic acid in a cell. The expression vector typically contains an origin of replication, a promoter, as well as specific genes that permit phenotypic selection of transformed cells.

Expression vectors containing a nucleic acid sequence of the invention can be prepared using well known methods and include a cDNA sequence encoding the polypeptide operably linked to suitable transcriptional or translational regulatory nucleotide sequences. Examples of regulatory sequences include transcriptional promoters, operators, or enhancers, mRNA ribosomal binding sites, and appropriate sequences which control transcription and translation initiation and termination. Nucleotide sequences are "operably linked" when the regulatory sequence functionally relates to the cDNA sequence of the invention. Expression vectors, regulatory elements and the construction thereof are well known in the art, and therefore are not limited to those recited above.

In addition, sequences encoding appropriate signal peptides that are not naturally associated with the polypeptides of the invention can be incorporated into expression vectors. For example, a DNA sequence for a signal peptide (secretory) leader can be fused in-frame to a nucleotide sequence of the invention so that the polypeptide of the invention is initially translated as a fusion protein comprising the signal peptide. A signal peptide that is functional in the intended host cells enhances extracellular secretion of the expressed polypeptide. The signal peptide can be cleaved from the polypeptide upon secretion from the cell. In some cases, signal peptides are cleaved in two or more stages; this is also within the scope of the invention where appropriate.

Fusions of additional peptide sequences at the amino and carboxyl terminal ends of the polypeptides of the invention can be used with the current invention.

In one embodiment, the invention includes a host cell comprising a nucleic acid of the invention. As used herein, the term "host cell" refers to a cell in which a vector can be propagated and its DNA expressed. The term also includes any progeny of the subject host cell. It is understood that all progeny may not be identical to the parental cell since there may be mutations that occur during replication. Such progeny are included when the term "host cell" is used. Methods of stable transfer where the foreign DNA is continuously maintained in the host are known in the art. Another embodiment of the invention is a method of making a recombinant host cell comprising introducing the vectors of the invention, into a host cell. In a further embodiment, a method of producing a polypeptide comprising culturing the host cells of the invention under conditions to produce the polypeptide is contemplated. In one embodiment the polypeptide is recovered.

Suitable host cells for expression of polypeptides of the invention are well known in the art, and include, but are not limited to, prokaryotes, yeast, higher eukaryotic cells, or combinations thereof. (See for example, Pouwels et al. Cloning Vectors: A Laboratory Manual, Elsevier, N.Y. (1985)). A particularly preferred host cell is yeast. Cell-free translation systems, also well known in the art, could also be employed to produce the disclosed polypeptides using RNAs derived from DNA constructs disclosed herein.

Host cells may be modified by any methods known in the art for gene transfer including, for example, the use of delivery devices such as lipids and viral vectors, naked DNA, electroporation and particle-mediated gene transfer.

Transformation of a host cell with recombinant DNA may be carried out by conventional techniques as are well known to those skilled in the art. Where the host is prokaryotic, such as *Escherichia coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used.

A variety of host-expression vector systems may be utilized to express proteins or polypeptides according to the present invention. These include but are not limited to microorganisms such as bacteria transformed with recombinant bacteriophage DNA, plasmid DNA or cosmid DNA expression vectors containing an appropriate coding sequence; yeast transformed with recombinant yeast expression vectors containing the appropriate coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing an appropriate coding sequence; insect cell systems infected with recombinant virus expression vectors (e.g., baculovirus) containing an appropriate coding sequence; or animal cell systems infected with recombinant virus expression vectors (e.g., retroviruses, adenovirus, vaccinia virus) containing an appropriate coding sequence, or transformed animal cell systems engineered for stable expression. In such cases where glycosylation may be important, expression systems that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, etc. may be used in the expression vector (see e.g., Bitter, et al., Methods in Enzymology, 153:516-544, 1987). For example, when cloning in bacterial systems, inducible promoters such as pL of bacteriophage λ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted polypeptide coding sequence.

In yeast, such as *Saccharomyces cerevisiae*, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast Saccharomyces, 1982, Eds. Strathem et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome. Cloning and expression in yeast is further described in T. A. Brown, "Gene Cloning and DNA Analysis"

(4th ed., Blackwell, 2001), pp. 286-288. Other species of yeast such as *Pichia pastoris* can be used.

In cases where plant expression vectors are used, the expression of a polypeptide coding sequence may be driven by any of a number of promoters. For example, viral promoters such as the 35S RNA and 19S RNA promoters of CaMV (Brisson, et al., Nature, 310:511-514, 1984), or the coat protein promoter to TMV (Takamatsu, et al., EMBO J., 6:307-311, 1987) may be used; alternatively, plant promoters such as the small subunit of RUBISCO (Coruzzi, et al., EMBO J. 3:1671-1680, 1984; Broglie, et al., Science 224:838-843, 1984); or heat shock promoters, e.g., soybean hsp17.5-E or hsp17.3-B (Gurley, et al., Mol. Cell. Biol., 6:559-565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, Methods for Plant Molecular Biology, Academic Press, NY, Section VIII, pp. 421-463, 1988; and Grierson & Corey, Plant Molecular Biology, 2d Ed., Blackie, London, Ch. 7-9, 1988.

An alternative expression system that can be used to express a protein of the invention is an insect system. In one such system, *Autographa californica* nuclear polyhedrosis virus (AcNPV) is used as a vector to express foreign genes. The virus grows in *Spodoptera frugiperda* cells. The polypeptide coding sequence may be cloned into non-essential regions (in *Spodoptera frugiperda*, for example, the polyhedrin gene) of the virus and placed under control of an AcNPV promoter (for example the polyhedrin promoter). Successful insertion of the polypeptide coding sequence will result in inactivation of the polyhedrin gene and production of non-occluded recombinant virus (i.e., virus lacking the proteinaceous coat coded for by the polyhedrin gene). These recombinant viruses are then used to infect cells in which the inserted gene is expressed. (E.g., see Smith, et al., J. Biol. 46:584, 1983; Smith, U.S. Pat. No. 4,215,051).

For long-term, high-yield production of recombinant proteins, stable expression is preferred. Rather than using expression vectors which contain viral origins of replication, host cells can be transformed with the cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in enriched media, and then are switched to a selective media. A number of selection systems may be used, including but not limited to the herpes simplex virus thymidine kinase (Wigler, et al., Cell 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes, which can be employed in tk$^-$, hgprt$^-$ or aprt$^-$ cells respectively. Also, antimetabolite resistance-conferring genes can be used as the basis of selection; for example, the genes for dhfr, which confer resistance to methotrexate (Wigler, et al., Natl. Acad. Sci. USA, 77:3567, 1980; O'Hare, et al., Proc. Natl. Acad. Sci. USA, 78:1527, 1981); gpt, which confers resistance to mycophenolic acid (Mulligan & Berg, Proc. Natl. Acad. Sci. USA, 78:2072, 1981; neo, which confers resistance to the aminoglycoside G418 (Colberre-Garapin, et al., J. Mol. Biol., 150:1, 1981); and hygro, which confers resistance to hygromycin (Santerre, et al., Gene, 30:147, 1984). Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:804, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory ed., 1987).

Isolation and purification of protein expressed in mammalian, plant, yeast, or bacterial cells may be carried out by conventional means including preparative chromatography and immunological separations involving monoclonal or polyclonal antibodies. Antibodies provided in the present invention are immunoreactive with a polypeptide according to the present invention. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., Nature, 256:495, 1975; Current Protocols in Molecular Biology, Ausubel, et al., ed., 1989).

A further embodiment of the invention is methods of making trehalose and its derivatives, for example, using the nucleotides and polypeptides of the invention.

Also within the practice of the invention is an organism (e.g., microorganism or plant) that is used to construct a platform for high level production of a substrate of trehalose synthases (e.g., maltose) and the introduction of a nucleic acid of the invention into the organism.

Unless otherwise indicated, nucleic acids of the invention that are DNA encompass both cDNA (DNA reverse transcribed from mRNA and lacking introns) and isolated genomic DNA (DNA that can contain introns.)

In one embodiment, the nucleic acids of the invention are used to create other nucleic acids coding for trehalose synthases. For example, the invention provides for a method of identifying a trehalose synthase comprising constructing a DNA library using the nucleic acids of the invention, screening the library for nucleic acids which encode for at least one trehalose synthase. The DNA library using the nucleic acids of the invention may be constructed by any process known in the art where DNA sequences are created using the nucleic acids of the invention as a starting point, including but not limited to DNA shuffling. In such a method, the library may be screened for trehalose synthases using a functional assay to find a target nucleic acid that encodes a trehalose synthase. The activity of a trehalose synthase may be analyzed using, for example, the methods described herein. In one embodiment, high throughput screening is utilized to analyze the activity of the encoded polypeptides.

As used herein a "nucleotide probe" is defined as an oligonucleotide or polynucleotide capable of binding to a target nucleic acid of complementary sequence through one or more types of chemical bonds, through complementary base pairing, or through hydrogen bond formation.

A "target nucleic acid" herein refers to a nucleic acid to which the nucleotide probe or molecule can specifically hybridize. The probe is designed to determine the presence or absence of the target nucleic acid, and the amount of target nucleic acid. The target nucleic acid has a sequence that is significantly complementary to the nucleic acid sequence of the corresponding probe directed to the target so that the probe and the target nucleic acid can hybridize. Preferably, the hybridization conditions are such that hybridization of the probe is specific for the target nucleic acid. As recognized by one of skill in the art, the probe may also contain additional nucleic acids or other moieties, such as labels, which may not specifically hybridize to the target. The term target nucleic acid may refer to the specific nucleotide sequence of a larger nucleic acid to which the probe is directed or to the overall sequence (e.g., gene or mRNA). One skilled in the art will recognize the full utility under various conditions.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value; however, inherently contains certain errors necessarily resulting from the standard deviation found in their respective testing measurements.

In one embodiment, the present invention relates to an isolated and purified nucleic acid sequence encoding a functional *Picrophilus torridus* trehalose synthase protein such that the protein has a catalytic activity of catalyzing the intramolecular rearrangement of the α1,4-linkage of maltose to the α1,1-linkage of trehalose, or vice versa.

In another embodiment, the present invention relates to an isolated and purified DNA sequence wherein the sequence is:

(SEQ ID NO: 1)

CATATGCTTGATAATAATGGTTTATGGTACCGTGATGCTGTATTTTATGAGGTTCCT

GTAAAATCATTCTATGATTCAAACAACGATGGCATAGGCGATTTTAATGGCCTAACA

ATGAAGCTTGACTATTTAAAAAAGCTTGGTGTTGACGCTTTATGGCTGCTGCCATTC

TATAAATCGCCATTGAAGGACGACGGTTATGATATATCTGATTACTATTCAATACTG

CCGGAGTATGGAACAATTGATGATTTTAAAAACTTCATAGATACCGCGCATTCAATG

AACATAAGGGTTATAGCGGACCTCGTTCTAAACCATGTATCTGACCAGCATCCATG

GTTCATTGAATCAAGAAGCAGCATTGATAATCCAAAGAGGGACTGGTTTATATGGA

GCGACACACCAGAAAAATTTAAGGAGGCAAGGATAATATTTATAGATACAGAAAAA

TCAAACTGGACCTATGATCCGGAAACAAAACAGTATTACTTTCACAGGTTTTACTCA

TCCCAGCCGGATCTTAACTATGACAATCCTGATGTCAGGAACGAGGTTAAAAAGGT

TATAAGGTACTGGCTTGACCTTGGTCTTGACGGCTTCAGGGCAGATGCGGTTCCAT

ACCTCTTTAAAAGGGAGAATACAAACTGTGAGAACCTGCCAGAAACACACAACTTC

TTTAAGGAAATAAGGAAGATGATGGATGAAGATTACCCTGGAACAATACTTTTAGCA

GAGGCAAACCAGTGGCCTACAGAAACAAAGGCATACTTTGGTAACGGCGATGAAT

TTCACATGGCATTCAATTTTCCTTTGATGCCAAGGATCTTTATAGCACTGGCCAGGA

GCGATTACTATCCAATAATGGATATAATAAAGCAGACGCTGCCGATACCTGATAAC

TGCGACTGGTGCATCTTTCTTAGAAACCATGACGAGCTTACCCTTGAGATGGTCAC

GGATTCAGAAAGGGATATCATGTACAGGGAGTACGCAAAGATACCAAAGATGCGTT

TAAATCTTGGAATAAGGCGCAGGCTAGCACCGCTTGCTGACAATGATATCAACACA

ATAGAACTATTAAACGCATTAATATTTTCACTGCCCGGCACGCCGATAATATACTAT

GGCGACGAGATAGGCATGGGTGATAACATATATCTTGGCGATAGAAACGGTGTGA

GAACGCCAATGCAGTGGAGCTATGATAGAAACGCAGGTTTCTCAATGGCAGATTC

GGAGCAGCTCTACTCACCGGTGATAACAAATCCTAATTATCATTATGAAAGCGTGA

ACGTTGAGGCTGAGCTCAGGCTGAGCTCATCGCTTTTAAACTGGATGATAAAGATT

ATACATGTTAGAAAGGATTACAAGGAGCTCCTCGGCCGCGGTTCAATAAAATTTAT

AGAGCAGGGTAATAAAAGGGTGCTTTCTTATATAAGAGAGTATGAAAACCAGAGGA

TGCTGTGCCTTTTTAATTTATCAAGGAATCCAACGTACGTTGAGCTAAATTTAAGTG

ATTACATAGGGCTTAAACCAATAGAGGCCATAACAAAGGCAGCATTTCCAAGGATA

```
AAGGATGATAGGTATTTCATAACAATGACACCAAGGTCATTCTTCTGGTTTAATTTA

ATTGTACCTGAAAGGGATGATTCATACGACCTCATTGGAGAAGATGCGAATTC.
```

In this embodiment as shown in SEQ ID NO: 1, characters in bold indicate sites that were modified according to the *E. coli* codon usage database to avoid NdeI digestion during cloning into vector pET-23a(+). Words underlined indicate sites that were changed due to mutation that resulted from PCR. The coding amino acids did not have to be altered in all modifications. Finally, GC were added in front of the EcoR I cutting site in order to generate an in-frame read His-tag.

In another embodiment, the present invention relates to an isolated and purified DNA sequence wherein the sequence is:

```
                                       (SEQ ID NO: 2)
ATGCTTGATAATAATGGTTTATGGTACCGTGATGCTGTATTTTATGAGGT

TCCTGTAAAATCATTCTATGATTCAAACAACGATGGCATAGGCGATTTTA

ATGGCCTAACAATGAAGCTTGACTATTTAAAAAAGCTTGGTGTTGACGCT

TTATGGCTGCTGCCATTCTATAAATCGCCATTGAAGGACGACGGTTATGA

TATATCTGATTACTATTCAATACTGCCGGAGTATGGAACAATTGATGATT

TTAAAAACTTCATAGATACCGCGCATTCAATGAACATAAGGGTTATAGCG

GACCTCGTTCTAAACCATGTATCTGACCAGCATCCATGGTTCATTGAATC

AAGAAGCAGCATTGATAATCCAAAGAGGGACTGGTTTATATGGAGCGACA

CACCAGAAAAATTTAAGGAGGCAAGGATAATATTTATAGATACAGAAAAA

TCAAACTGGACCTATGATCCGGAAACAAAACAGTATTACTTTCACAGGTT

TTACTCATCCCAGCCGGATCTTAACTATGACAATCCTGATGTCAGGAACG

AGGTTAAAAAGGTTATAAGGTACTGGCTTGACCTTGGTCTTGACGGCTTC

AGGGCAGATGCGGTTCCATACCTCTTTAAAAGGGAGAATACAAACTGTGA

GAACCTGCCAGAAACACACAACTTCTTTAAGGAAATAAGGAAGATGATGG

ATGAAGATTACCCTGGAACAATACTTTTAGCAGAGGCAAACCAGTGGCCT

ACAGAAACAAAGGCATACTTTGGTAACGGCGATGAATTTCACATGGCATT

CAATTTTCCTTTGATGCCAAGGATCTTTATAGCACTGGCCAGGAGCGATT

ACTATCCAATAATGGATATAATAAAGCAGACGCTGCCGATACCTGATAAC

TGCGACTGGTGCATCTTTCTTAGAAACCATGACGAGCTTACCCTTGAGAT

GGTCACGGATTCAGAAAGGGATATCATGTACAGGGAGTACGCAAAGATAC

CAAAGATGCGTTTAAATCTTGGAATAAGGCGCAGGCTAGCACCGCTTGCT

GACAATGATATCAACACAATAGAACTATTAAACGCATTAATATTTTCACT

GCCCGGCACGCCGATAATATACTATGGCGACGAGATAGGCATGGGTGATA

ACATATATCTTGGCGATAGAAACGGTGTGAGAACGCCAATGCAGTGGAGC

TATGATAGAAACGCAGGTTTCTCAATGGCAGATTCGGAGCAGCTCTACTC

ACCGGTGATAACAAATCCTAATTATCATTATGAAAGCGTGAACGTTGAGG

CTGAGCTCAGGCTGAGCTCATCGCTTTTAAACTGGATGATAAAGATTATA

CATGTTAGAAAGGATTACAAGGAGCTCCTCGGCCGCGGTTCAATAAAATT

TATAGAGCAGGGTAATAAAAGGGTGCTTTCTTATATAAGAGAGTATGAAA
```

```
ACCAGAGGATGCTGTGCCTTTTTAATTTATCAAGGAATCCAACGTACGTT

GAGCTAAATTTAAGTGATTACATAGGGCTTAAACCAATAGAGGCCATAAC

AAAGGCAGCATTTCCAAGGATAAAGGATGATAGGTATTTCATAACAATGA

CACCAAGGTCATTCTTCTGGTTTAATTTAATTGTACCTGAAAGGGATGAT

TCATACGACCTCATTGGAGAAGATGCGAATTCCCGGGTCGACAAGCTTGC

GGCCGCACTCGAGCACCACCACCACCACCACTGA.
```

In SEQ ID NO: 2, the sequence encodes a recombinant *Picrophilus torridus* trehalose synthase protein that includes, at its carboxyl-terminus, a linker plus six codons encoding histidine residues to generate a hexahistidine purification tag as is generally known in the art. Start and stop codons for SEQ ID NO: 2 are underlined.

In yet another embodiment, the present invention relates to an isolated and purified DNA sequence wherein the sequence encodes a protein of the sequence:

```
                                       (SEQ ID NO: 3)
MLDNNGLWYRDAVFYEVPVKSFYDSNNDGIGDFNGLTMKLDYLKKLGVD

ALWLLPFYKSPLKDDGYDISDYYSILPEYGTIDDFKNFIDTAHSMNIRV

IADLVLNHVSDQHPWFIESRSSIDNPKRDWFIWSDTPEKFKEARIIFID

TEKSNWTYDPETKQYYFHRFYSSQPDLNYDNPDVRNEVKKVIRYWLDLG

LDGFRADAVPYLFKRENTNCENLPETHNFFKEIRKMMDEDYPGTILLAE

ANQWPTETKAYFGNGDEFHMAFNFPLMPRIFIALARSDYYPIMDIIKQT

LPIPDNCDWCIFLRNHDELTLEMVTDSERDIMYREYAKIPKMRLNLGIR

RRLAPLADNDINTIELLNALIFSLPGTPIIYYGDEIGMGDNIYLGDRNG

VRTPMQWSYDRNAGFSMADSEQLYSPVITNPNYHYESVNVEAELRLSSS

LLNWMIKIIHVRKDYKELLGRGSIKFIEQGNKRVLSYIREYENQRMLCL

FNLSRNPTYVELNLSDYIGLKPIEAITKAAFPRIKDDRYFITMTPRSFF

WFNLIVPERDDSYDLIGED.
```

This is the wild-type *Picrophilus torridus* trehalose synthase protein without the linker and without the hexahistidine purification tag.

In yet another embodiment, the present invention relates to an isolated and purified DNA sequence wherein the sequence encodes a protein of the sequence:

(SEQ ID NO: 4)
MLDNNGLWYRDAVFYEVPVKSFYDSNNDGIGDFNGLTMKLDYLKKLGVDALWLLPFY

KSPLKDDGYDISDYYSILPEYGTIDDFKNFIDTAHSMNIRVIADLVLNHVSDQHPWFIESR

SSIDNPKRDWFIWSDTPEKFKEARIIFIDTEKSNWTYDPETKQYYFHRFYSSQPDLNYD

NPDVRNEVKKVIRYWLDLGLDGFRADAVPYLFKRENTNCENLPETHNFFKEIRKMMDE

DYPGTILLAEANQWPTETKAYFGNGDEFHMAFNFPLMPRIFIALARSDYYPIMDIIKQTL

PIPDNCDWCIFLRNHDELTLEMVTDSERDIMYREYAKIPKMRLNLGIRRRLAPLADNDIN

TIELLNALIFSLPGTPIIYYGDEIGMGDNIYLGDRNGVRTPMQWSYDRNAGFSMADSEQ

LYSPVITNPNYHYESVNVEAELRLSSSLLNWMIKIIHVRKDYKELLGRGSIKFIEQGNKR

VLSYIREYENQRMLCLFNLSRNPTYVELNLSDYIGLKPIEAITKAAFPRIKDDRYFITMTP

RSFFWFNLIVPERDDSYDLIGED|ANSRVDKLAAALE|HHHHHH.

The protein of SEQ ID NO: 4 includes the linker, which is boxed in the sequence, as well as the hexahistidine purification tag.

In another embodiment, the present invention relates to an isolated and purified nucleic acid sequence encoding a functional *Picrophilus torridus* trehalose synthase protein, wherein the sequence is a nucleic acid sequence that is at least 95% identical to SEQ ID NO: 1 or SEQ ID NO: 2, provided that the nucleic acid sequence is translated into a protein encoding a functional *Picrophilus torridus* trehalose synthase protein such that the protein has a catalytic activity of catalyzing the intramolecular rearrangement of the α1,4-linkage of maltose to the α1,1-linkage of trehalose, or vice versa. Preferably, the nucleic acid sequence is at least 97.5% identical to SEQ ID NO: 1 or SEQ ID NO: 2. More preferably, the nucleic acid sequence is at least 99% identical to SEQ ID NO: 1 or SEQ ID NO: 2.

In another embodiment, the present invention relates to an isolated and purified DNA sequence encoding a functional *Picrophilus torridus* trehalose synthase protein, wherein the DNA sequence is selected from the group consisting of:
(a) SEQ ID NO: 1; and
(b) a DNA sequence encoding a protein differing by from one to 20 conservative amino acid substitutions from SEQ ID NO: 3, wherein the protein encoded is a functional *Picrophilus torridus* trehalose synthase protein such that the protein has a catalytic activity of catalyzing the intramolecular rearrangement of the α1,4-linkage of maltose to the α1,1-linkage of trehalose, or vice versa, and wherein a conservative amino acid substitution is one of the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. Typically, the DNA sequence encodes a protein differing by from one to 10 conservative amino acid substitutions from SEQ ID NO: 3. Preferably, the DNA sequence encodes a protein differing by from one to five conservative amino acid substitutions from SEQ ID NO: 3. More preferably, the DNA sequence encodes a protein differing by from one to two conservative amino acid substitutions from SEQ ID NO: 3. Preferably, the conservative amino acid substitutions do not occur at Asp$^{203}$, Glu$^{245}$, Asp$^{311}$, His$^{106}$ or His$^{310}$.

Similarly, the present invention also relates to an isolated and purified DNA sequence encoding a functional *Picrophilus torridus* trehalose synthase protein, wherein the DNA sequence is selected from the group consisting of:
(a) SEQ ID NO: 2; and
(b) a DNA sequence encoding a protein differing by from one to 20 conservative amino acid substitutions from SEQ ID NO: 4, wherein the protein encoded is a functional *Picrophilus torridus* trehalose synthase protein such that the protein has a catalytic activity of catalyzing the intramolecular rearrangement of the α1,4-linkage of maltose to the α1,1-linkage of trehalose, or vice versa, and wherein a conservative amino acid substitution is one of the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. Typically, the DNA sequence encodes a protein differing by from one to 10 conservative amino acid substitutions from SEQ ID NO: 4. Preferably, the DNA sequence encodes a protein differing by from one to five conservative amino acid substitutions from SEQ ID NO: 4. More preferably, the DNA sequence encodes a protein differing by from one to two conservative amino acid substitutions from SEQ ID NO: 4. Preferably, the conservative amino acid substitutions do not occur at residues corresponding to residues identified as Asp$^{203}$, Glu$^{245}$, Asp$^{311}$, His$^{106}$ or His$^{310}$ in wild-type *Picrophilus torridus* trehalose synthase protein.

In yet another embodiment, the present invention relates to a vector comprising an isolated and purified DNA sequence encoding a functional *Picrophilus torridus* trehalose synthase protein such that the protein has a catalytic activity of successfully catalyzing the intramolecular rearrangement of the α1,4-linkage of maltose to the α1,1-linkage of trehalose, or vice versa.

In another embodiment, the present invention relates to a vector comprising an isolated and purified DNA sequence encoding a functional *Picrophilus torridus* trehalose synthase protein, wherein the sequence is SEQ ID NO: 1 or SEQ ID NO: 2.

In another embodiment, the present invention relates to a vector comprising an isolated and purified DNA sequence encoding a functional *Picrophilus torridus* trehalose synthase protein, wherein the sequence encodes a protein of the sequence SEQ ID NO: 3 or SEQ ID NO: 4.

In yet another embodiment, the present invention relates to a vector comprising an isolated and purified DNA sequence encoding a functional *Picrophilus torridus* trehalose synthase protein, wherein the sequence is at least 95% identical to SEQ ID NO: 1 or SEQ ID NO: 2. Preferably, the sequence is at least 97.5% identical to SEQ ID NO: 1 or SEQ ID NO: 2. More preferably, the sequence is at least 99% identical to SEQ ID NO: 1 or SEQ ID NO: 2.

In another embodiment, the present invention relates to a vector comprising an isolated and purified DNA sequence encoding a functional *Picrophilus torridus* trehalose synthase protein, wherein the sequence is selected from the group consisting of:
(a) SEQ ID NO: 1; and
(b) a DNA sequence encoding a protein differing by from one to 20 conservative amino acid substitutions from SEQ ID NO: 3, wherein the protein encoded is a functional *Picrophilus torridus* trehalose synthase protein such that the protein has a catalytic activity of catalyzing the intramolecular rearrangement of the α1,4-linkage of maltose to the α1,1-linkage of trehalose, or vice versa, and wherein a conservative amino acid substitution is one of the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. As described above, typically, the DNA sequence encodes a protein differing by from one to 10 conservative amino acid substitutions from SEQ ID NO: 3. Preferably, the DNA sequence encodes a protein differing by from one to five conservative amino acid substitutions from SEQ ID NO: 3. More preferably, the DNA sequence encodes a protein differing by from one to two conservative amino acid substitutions from SEQ ID NO. 3. Preferably, the conservative amino acid substitutions do not occur at $Asp^{203}$, $Glu^{245}$, $Asp^{311}$, $His^{106}$ or $His^{310}$.

In yet another embodiment, the present invention relates to a vector comprising an isolated and purified DNA sequence encoding a functional *Picrophilus torridus* trehalose synthase protein, wherein the sequence is selected from the group consisting of:
(a) SEQ ID NO: 2; and
(b) a DNA sequence encoding a protein differing by from one to 20 conservative amino acid substitutions from SEQ ID NO: 4, wherein the protein encoded is a functional *Picrophilus torridus* trehalose synthase protein such that the protein has a catalytic activity of catalyzing the intramolecular rearrangement of the α1,4-linkage of maltose to the α1,1-linkage of trehalose, or vice versa, and wherein a conservative amino acid substitution is one of the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. As described above, typically, the DNA sequence encodes a protein differing by from one to 10 conservative amino acid substitutions from SEQ ID NO: 4. Preferably, the DNA sequence encodes a protein differing by from one to five conservative amino acid substitutions from SEQ ID NO: 4. More preferably, the DNA sequence encodes a protein differing by from one to two conservative amino acid substitutions from SEQ ID NO. 4. Preferably, the conservative amino acid substitutions do not occur at residues corresponding to residues identified as $Asp^{203}$, $Glu^{245}$, $Asp^{311}$, $His^{106}$ or $His^{310}$ in wild-type *Picrophilus torridus* trehalose synthase protein.

In another embodiment, the present invention relates to a host cell transformed or transfected with a vector comprising an isolated and purified DNA sequence encoding a functional *Picrophilus torridus* trehalose synthase protein such that the protein has a catalytic activity of catalyzing the intramolecular rearrangement of the α1,4-linkage of maltose to the α1,1-linkage of trehalose, or vice versa.

In another embodiment, the present invention relates to a host cell transformed or transfected with a vector comprising an isolated and purified DNA sequence encoding a functional *Picrophilus torridus* trehalose synthase protein, wherein the sequence is SEQ ID NO: 1 or SEQ ID NO: 2.

In yet another embodiment, the present invention relates to a host cell transformed or transfected with a vector comprising an isolated and purified DNA sequence encoding a functional *Picrophilus torridus* trehalose synthase protein, wherein the sequence encodes a protein of the sequence SEQ ID NO: 3 or SEQ ID NO: 4.

In another embodiment, the present invention relates to a host cell transformed or transfected with a vector comprising an isolated and purified DNA sequence encoding a functional *Picrophilus torridus* trehalose synthase protein, wherein the sequence is at least 95% identical to SEQ ID NO: 1 or SEQ ID NO: 2. Preferably, the sequence is at least 97.5% identical to SEQ ID NO: 1 or SEQ ID NO: 2. More preferably, the sequence is at least 99% identical to SEQ ID NO: 1 or SEQ ID NO: 2.

In yet another embodiment, the present invention relates to a host cell transformed or transfected with a vector comprising an isolated and purified DNA sequence encoding a functional *Picrophilus torridus* trehalose synthase protein, wherein the sequence is selected from the group consisting of:
(a) SEQ ID NO: 1; and
(b) a DNA sequence encoding a protein differing by from one to 20 conservative amino acid substitutions from SEQ ID NO: 3, wherein the protein encoded is a functional *Picrophilus torridus* trehalose synthase protein such that the protein has a catalytic activity of catalyzing the intramolecular rearrangement of the α1,4-linkage of maltose to the α1,1-linkage of trehalose, or vice versa, and wherein a conservative amino acid substitution is one of the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. As described above, typically, the DNA sequence encodes a protein differing by from one to 10 conservative amino acid substitutions from SEQ ID NO: 3. Preferably, the DNA sequence encodes a protein differing by from one to five conservative amino acid substitutions from SEQ ID NO: 3. More preferably, the DNA sequence encodes a protein differing by from one to two conservative amino acid substitutions from SEQ ID NO. 3. Preferably, the conservative amino acid substitutions do not occur at $Asp^{203}$, $Glu^{245}$, $Asp^{311}$, $His^{106}$ or $His^{310}$.

In still another embodiment, the present invention relates to a host cell transformed or transfected with a vector comprising an isolated and purified DNA sequence encoding a functional *Picrophilus torridus* trehalose synthase protein, wherein the sequence is selected from the group consisting of:
(a) SEQ ID NO: 2; and
(b) a DNA sequence encoding a protein differing by from one to 20 conservative amino acid substitutions from SEQ ID NO: 4, wherein the protein encoded is a functional *Picrophilus torridus* trehalose synthase protein such that the protein has a catalytic activity of catalyzing the intramolecular rearrangement of the α1,4-linkage of maltose to the α1,1-linkage of trehalose, or vice versa, and wherein a conservative amino acid substitution is one of the following substitutions: Ala/

Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. As described above, typically, the DNA sequence encodes a protein differing by from one to 10 conservative amino acid substitutions from SEQ ID NO: 4. Preferably, the DNA sequence encodes a protein differing by from one to five conservative amino acid substitutions from SEQ ID NO: 4. More preferably, the DNA sequence encodes a protein differing by from one to two conservative amino acid substitutions from SEQ ID NO: 4. Preferably, the conservative amino acid substitutions do not occur at residues corresponding to residues identified as $Asp^{203}$, $Glu^{245}$, $Asp^{311}$, $His^{106}$ or $His^{310}$ in wild-type Picrophilus torridus trehalose synthase protein.

In another embodiment, the present invention relates to a method of producing an isolated protein having Picrophilus torridus trehalose synthase protein activity such that the protein has a catalytic activity of catalyzing the intramolecular rearrangement of the α1,4-linkage of maltose to the α1,1-linkage of trehalose, or vice versa, comprising the steps of:
(a) culturing the host cell under conditions wherein a protein having Picrophilus torridus trehalose synthase activity is expressed by the host cell; and
(b) isolating the protein having Picrophilus torridus trehalose synthase activity so that isolated protein is produced.

In another embodiment, the present invention relates to an isolated and purified protein molecule having functional Picrophilus torridus trehalose synthase activity such that the protein has a catalytic activity of catalyzing the intramolecular rearrangement of the α1,4-linkage of maltose to the α1,1-linkage of trehalose, or vice versa.

In another embodiment, the present invention relates to an isolated and purified protein molecule having functional Picrophilus torridus trehalose synthase activity such that the protein has a catalytic activity of catalyzing the intramolecular rearrangement of the α1,4-linkage of maltose to the α1,1-linkage of trehalose, or vice versa, wherein the protein has the amino acid sequence of SEQ ID NO: 3.

In another embodiment, the present invention relates to an isolated and purified protein molecule having functional Picrophilus torridus trehalose synthase activity such that the protein has a catalytic activity of catalyzing the intramolecular rearrangement of the α1,4-linkage of maltose to the α1,1-linkage of trehalose, or vice versa, wherein the protein has the amino acid sequence of SEQ ID NO: 4. Also within the scope of the present invention are isolated and purified protein molecules having functional Picrophilus torridus trehalose synthase activity such that the protein has a catalytic activity of catalyzing the intramolecular rearrangement of the α1,4-linkage of maltose to the α1,1-linkage of trehalose, or vice versa, wherein the protein has an amino acid sequence varying from the amino acid sequence of SEQ ID NO: 4 by one or more of the following: (1) greater or lesser numbers of histidine residues at the carboxyl terminus of the protein; or (2) alteration of the sequence of the linker; and (3) removal of the linker. With respect to (1), although in one application the use of a hexahistidine (6 histidine) purification tag is optimum, greater or lesser numbers of histidine residues can be incorporated in the purification tag. For example, and not by way of limitation, the purification tag can incorporate 2, 3, 4, 5, 7, 8, 9, 10, 11, 12, 13, 14, 15, or more histidine residues, for example 20, 25, or 30 residues. The sequence of the linker can be altered, such as by conservative amino acid substitutions as described above, or by deleting or adding amino acid residues. The sequence of the linker provided above is ANSRVDKLAAALE.

In yet another embodiment, the present invention relates to an isolated and purified protein molecule having functional Picrophilus torridus trehalose synthase activity such that the protein has a catalytic activity of catalyzing the intramolecular rearrangement of the α1,4-linkage of maltose to the α1,1-linkage of trehalose, or vice versa, wherein the protein has an amino acid sequence selected from the group consisting of:
(a) the amino acid sequence of SEQ ID NO: 3; and
(b) an amino acid sequence differing by from one to 20 conservative amino acid substitutions from SEQ ID NO: 3 wherein a conservative amino acid substitution is one of the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. As described above, typically, the protein having conservative amino acid substitutions differs by from one to 10 conservative amino acid substitutions from SEQ ID NO: 3. Preferably, the protein having conservative amino acid substitutions differs by from one to five conservative amino acid substitutions from SEQ ID NO: 3. More preferably, the protein having conservative amino acid substitutions differs by from one to two conservative amino acid substitutions from SEQ ID NO: 3. Preferably, the conservative amino acid substitutions do not occur at $Asp^{203}$, $Glu^{245}$, $Asp^{311}$, $His^{106}$ or $His^{310}$.

In still another embodiment, the present invention relates to an isolated and purified protein molecule having functional Picrophilus torridus trehalose synthase activity such that the protein has a catalytic activity of catalyzing the intramolecular rearrangement of the α1,4-linkage of maltose to the α1,1-linkage of trehalose, or vice versa, wherein the protein has an amino acid sequence selected from the group consisting of:
(a) the amino acid sequence of SEQ ID NO: 4; and
(b) an amino acid sequence differing by from one to 20 conservative amino acid substitutions from SEQ ID NO: 4 wherein a conservative amino acid substitution is one of the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. As described above, typically, the protein having conservative amino acid substitutions differs by from one to 10 conservative amino acid substitutions from SEQ ID NO: 4. Preferably, the protein having conservative amino acid substitutions differs by from one to five conservative amino acid substitutions from SEQ ID NO: 4. More preferably, the protein having conservative amino acid substitutions differs by from one to two conservative amino acid substitutions from SEQ ID NO. 4. Preferably, the conservative amino acid substitutions do not occur at residues corresponding to residues identified as $Asp^{203}$, $Glu^{245}$, $Asp^{311}$, $His^{106}$ or $His^{310}$ in wild-type Picrophilus torridus trehalose synthase protein.

In another embodiment, the present invention relates to a method of producing trehalose comprising the step of reacting an isolated and purified protein molecule according to the present invention as described above and having functional Picrophilus torridus trehalose synthase activity with maltose under conditions in which the protein molecule catalyzes the intramolecular rearrangement of the α1,4-linkage of maltose to the α1,1-linkage of trehalose. Any of the isolated and purified protein molecules described above as being within the scope of the present invention can be used in this method, including isolated and purified protein molecules of SEQ ID NO: 3, SEQ ID NO: 4, or other variants or muteins of these protein molecules, including, but not limited to, protein molecules derived from SEQ ID NO: 3 or SEQ ID NO: 4 by conservative amino acid substitutions, or, in the case of SEQ ID NO: 4, by modification of the linker or hexahistidine purification tag.

As described further below in the Examples, another aspect of the present invention is a method for producing a mutein of *Picrophilus torridus* trehalose synthase with at least one altered property selected from the group consisting of regiospecificity and stereospecificity comprising the steps of:

(1) threading the wild-type *Picrophilus torridus* trehalose synthase amino acid sequence onto the three-dimensional structure of a mammalian analogue enzyme;

(2) docking at least one maltose substrate into the predicted active site pocket;

(3) mapping amino acid residues within a defined distance of the modeled substrate molecules and rationalizing the amino acid residues with predicted chemical transformations catalyzed by the *Picrophilus torridus* trehalose synthase to identify amino acid residues capable of steric, ionic, electronic and hydrophobic interactions with the substrate molecules;

(4) selecting at least one altered amino acid residue for its potential for substrate binding and positioning of the substrate molecule relative to the heme-catalytic center; and (5) introducing the at least one altered amino acid amino acid residue by site-directed mutagenesis to produce the mutein.

The property to be altered can be, but is not limited to, specificity of the catalytic reaction being carried out, $V_{max}$ of the reaction catalyzed, or $K_m$ for binding of the substrate.

Intramolecular rearrangement of the α1,4-linkage of maltose to the α1,1-linkage of trehalose catalyzed by *Picrophilus torridus* trehalose synthase yields trehalose, a valuable compound commercially used in the pharmaceutical, cosmetic, and food industries. As discussed above, currently known trehalose synthases lack heat and acidity resistant qualities which limits their applicability to scalable commercial production of trehalose from maltose. The biosynthetic utility of previously known trehalose synthases is severely limited by their lack of heat and acid resistance, since industrial biosynthesis of trehalose from maltose is likely to involve temperatures and pH ranges at which the enzymatic activity of prior art trehalose synthases diminishes severely or disappears completely. Moreover, the heat resistant and acid resistant trehalose synthase of the present invention offers a significant advantage for industrial production of trehalose by increasing the solubility of substrate and reducing the risk of contamination during production.

The *Picrophilus torridus* trehalose synthase gene now provides an alternative method for the reliable and cost effective production of trehalose, for example the expression of a *Picrophilus torridus* trehalose synthase gene in transgenic plants or microbial cells could providing for large scale production of trehalose.

We are also claiming the utility of selective, site-directed mutagenesis of the *Picrophilus torridus* trehalose synthase gene as a means for generating new biosynthetic capabilities in the resulting mutant enzyme.

The invention is described by the following Examples These Examples are for illustrative purposes only and are not intended to limit the invention.

EXAMPLES

Materials and Methods

Materials. All saccharides were purchased from Sigma Chemical Co. Column for protein purification was obtained from Amersham Pharmacia Biotech Inc. (Piscataway, N.J.). Acetonitrile was from TEDIA Company Inc. (U.S.A). All other chemicals and reagents were of analytical grade.

Bacterial Strains and Plasmids. The expression vector pET-23a(+) (Novagen, Madison, Wis.) was used and transformed into the *E. coli* strains DH5α and Rosetta-gami B (DE3) (Novagen) for cloning and expression, respectively. *E. coli* strains were cultured in Luria-Bertani (LB) broth and on LB agar supplemented with 100 μg/mL ampicillin (LB-Amp) for cloning host, or in combination with 15 μg/mL kanamycin, 12.5 μg/mL tetracycline, and 34 μg/mL chloramphenicol (LB-Amp-Kan-Tet-Chl) for expression host. All *E. coli* strains were cultured at 37° C. and in an orbital shaker at a speed of 225 rpm unless otherwise mentioned.

Example 1

Synthesis of Trehalose Synthase Gene

According to the published DNA sequence of the trehalose synthase gene of *Picrophilus torridus* (DSM 9790) (GenBank accession number AE017261) (PTTS) (24), 36 oligonucleotides were designed accounting for both strands of the full-length ORF of PTTS (1677 bp). Each oligonucleotide contained 70 base pairs and overlapped with adjacent ones by 20 base pairs. NdeI and EcoRI cutting sites were introduced into the 5' and 3' ends of the gene, respectively, and the three NdeI cutting sites inside the sequence were modified according to the *E. coli* codon usage database (at Website http://www.kazusa.or.jp/codon) without changing the amino acid sequence. The stop codon of PTTS was eliminated in order to in-frame read a His(6)-tag on the C terminal of the protein for one-step purification. Overlap extension PCR was used to assemble the 36 oligonucleotides to obtain the full-length PTTS gene. The synthesized PTTS gene were then digested with restriction enzymes NdeI and EcoRI and ligated into vector pET-23a(+). The resulting plasmid was transformed into Rosetta-gami B (DE3) for expression.

Example 2

Protein Purification

The strain harboring the plasmid was cultivated overnight in LB-Amp-Kan-Tet-Chl medium and refreshed in a ratio of 1:40 with the same medium. Protein expression was performed by using basal-level expression and the refreshed culture was cultivated at 27° C. and in an orbital shaker at a speed of 225 rpm for two days without the addition of IPTG. The culture broth was centrifuged at 4000 rpm for 10 min at 4° C. and the supernatant was decanted. The resulting cell pellet was resuspended in 20 mM sodium phosphate buffer (pH 7.0), and cells were lysed using a sonicator (Misonix, model XL-2020) set to power of 5% for 20 times of 30 s bursts, with a 30 s intermission between each burst. After centrifugation at 12000 rpm for 20 min, the supernatant containing crude enzyme was collected and then purified according to the following procedures: 20 mM sodium phosphate (pH 7.0) buffer containing 2.5 M NaCl and 25 mM imidazole was added to the crude extract to reach a final concentration of 0.5 M NaCl and 5 mM imidazole. It was then loaded onto a HiTrap Chelating HP column (1 mL) equilibrated with 20 mM sodium phosphate buffer (pH 7.0) containing 0.5 M NaCl and 5 mM imidazole on a fast protein liquid chromatography system (Pharmacia). After the column was washed, the PTTS was eluted with a linear gradient of 5 to 500 mM imidazole in the same buffer. Active fractions were pooled, concentrated and buffer exchanged using Centricon PL-30 (Amicon, Beverly, Mass.). The purified enzyme was stored in 20 mM sodium phosphate buffer (pH 7.0) and was analyzed on 12% SDS-PAGE.

Example 3

Protein Assay

Protein concentration was measured by the method of Bradford using a protein assay kit purchased from Bio-Rad Lab (Hercules, Calif.) with bovine serum albumin as standard.

Example 4

Enzyme Assay

The activity of PTTS was assayed by measuring the amount of trehalose produced from maltose. The standard reaction was performed by adding 1.5 µL purified enzyme into 50 µL reaction solution containing 50 mM sodium phosphate (pH 6.0) and 150 mM maltose and incubating in a 45° C. water bath for 25 min. The assay time was under the linear range of enzyme reaction. The reaction was terminated by heating the mixture in boiling water for 15 min. One unit of enzyme activity was defined as the amount of enzyme that catalyzes the formation of 1 µmol of trehalose per min. Kinetic analysis was performed under conditions of pH 6.0 and 45° C. for 5 min in 50 mM sodium phosphate buffer containing substrate (maltose, trehalose, or maltose plus a constant 10 mM of glucose) at various concentrations. The resulting data were analyzed offline with Origin 6.0 software (Microcal, Northampton, Mass.). All experiments were carried out in duplicate or triplicate.

Example 5

Carbohydrates Analysis

The amount of trehalose, glucose, and maltose after each enzymatic reaction was measured using a high performance liquid chromatography (HPLC) (SFD 2100) system equipped with an RI detector (Schambeck S F D, RI 2000) at a flow rate of 0.9 mL/min. A carbohydrate analysis column (HYPERSIL-100 Amino, Thermo Hypersil-Keystone) equilibrated with 75% acetonitrile, 24% Milli-Q water, and 1% formic acid was used. The retention times of glucose, maltose, and trehalose were 8.0, 11.2, and 12.5 min, respectively.

Results

Purification of Recombinant PTTS. The production of recombinant PTTS constituted a very high percentage, approximately 28% of the total cell protein. Protein purification was carried out by Ni-column and the enzyme was purified 3.6 fold with a yield of 63% and the specific activity was 80 units per mg of protein. SDS-PAGE analysis of the purified enzyme showed a single protein band around 65 kDa in size (FIG. 1).

Figure 2:
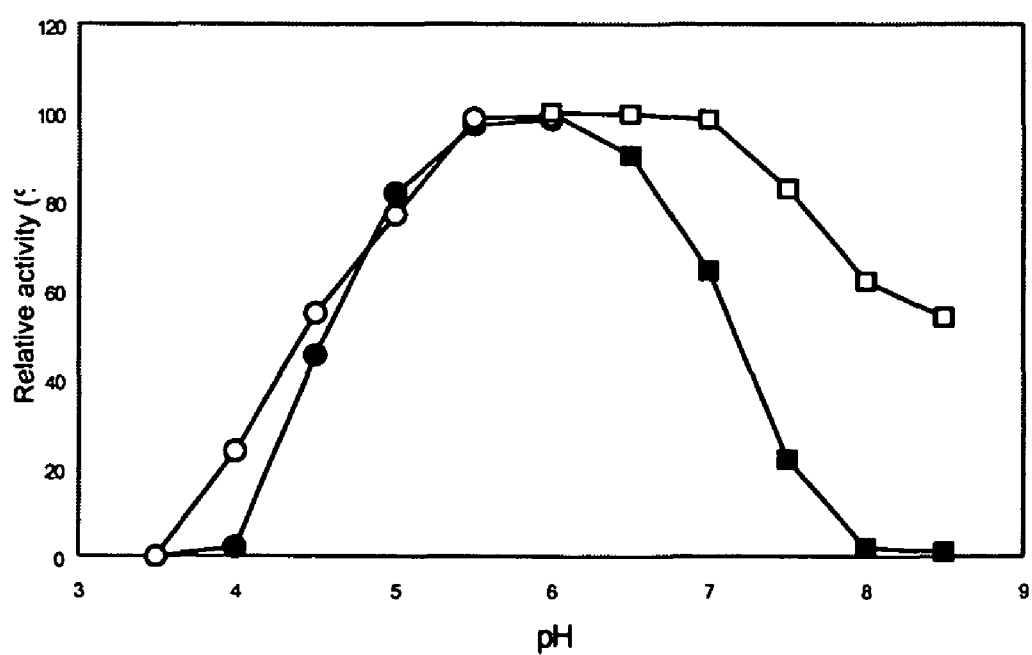
FIG. 2 is a graph which illustrates the effects of pH on the activity and stability of *Picrophilus torridus* trehalose synthase. The enzyme activities at various pH levels were examined at the maltose concentration of 150 mM and temperature of 45° C. for 25 min. The pH stability of *Picrophilus torridus* trehalose synthase enzyme was examined by measuring the residual activity of enzyme at pH 6.0 after pre-incubation in various pH levels at 45° C. for 20 min. The solid square (■) and circle (●) notations indicate the enzyme activity under 50 mM sodium phosphate buffer (pH 6.0~8.5) and 50 mM acetate buffer (pH 3.5~6.0), respectively. The open square (□) and circle (○) notations represent the pH stability under 50 mM sodium phosphate buffer (pH 6.0~8.5) and 50 mM acetate buffer (pH 3.5~6.0), respectively.
Figure 3:
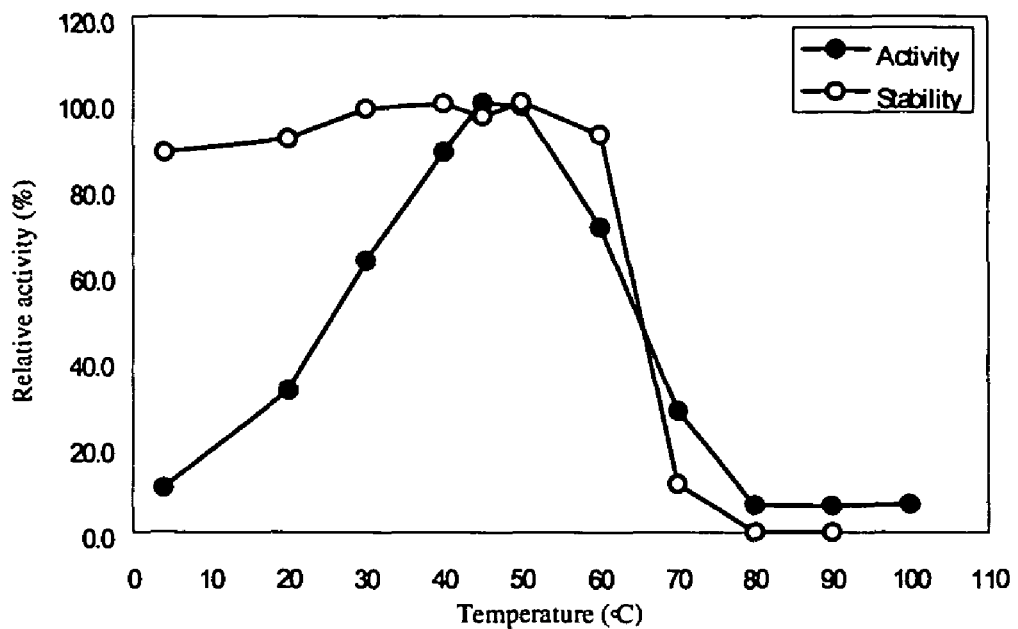
FIG. 3 is a graph which illustrates the effects of temperature on the activity and stability of *Picrophilus torridus* trehalose synthase. The enzyme activities at various temperatures were examined at the maltose concentration of 150 mM and pH 6.0 for 25 min. To examine temperature stability, the residual activity of the enzyme was measured at 45° C. after pre-incubation of the purified enzyme at different temperatures (4° C.~100° C.) and pH 6.0 for 20 min. The solid circle (●) and open circle (○) notations denote the enzyme activity and temperature stability, respectively, under various temperatures.

Effects of pH and Temperature on the Activity and Stability of Recombinant PTTS. The pH dependence of PTTS was studied at 45° C. in 50 mM acetate buffer (pH 3.5-6.0) or 50 mM phosphate buffer (pH 6.0-8.5) using 150 mM maltose as a substrate. The optimum pH for PTTS was 6.0 but the enzyme still maintained high activity at pH 5.0. pH stability, examining by pre-incubating the purified enzyme at various pH values for 20 min and then assaying the remaining enzyme activity under standard assay condition, showed a highly retained activity within a pH range of 5.0 to 7.5 (FIG. 2). The effects of temperature on PTTS activity and stability are depicted in FIG. 3. The optimum temperature was 45° C. and the enzyme maintained stability up to 60° C. at pH 6.0 for 20 min.

Kinetics Analysis. Kinetic parameters of PTTS were investigated at pH 6.0 and 45° C. for 5 min using maltose or trehalose as substrate (FIG. 7). The results showed that this enzyme has a much higher affinity for maltose than trehalose since the $K_M$ for trehalose was about five times that for maltose. Though a higher $k_{cat}$ for trehalose was seen, PTTS had a 2.5-fold higher enzyme efficiency ($k_{cat}/K_M$) toward maltose than trehalose. Moreover, it was found that the addition of glucose into the reaction mixture would retard trehalose formation, and this effect was proportional to the glucose concentration. In the presence of 10 mM glucose, PTTS showed a 3.3-fold increase in $K_M$ and a nearly unchanged $V_{max}$ for maltose, implying glucose as a competitive inhibitor of TSase (FIG. 7). This kinetic data is useful for determining the baseline activity of the enzyme and enables one of skill in the art to use this activity as a criterion for the isolation or construction of variants having substantially equivalent enzymatic activity.

Effects of Metal Ions and Reagents on PTTS Activity. The effects of metal ions and reagents were determined by examining enzyme activity in the presence of 1 mM and 10 mM metal ions or reagents under standard assay conditions (FIG. 8). The results indicated that the enzyme activity was inhibited strongly by $Ag^+$, $Hg^{2+}$, $Al^{3+}$, and SDS, and moderately by $Cd^{2+}$, $Cu^{2+}$, $Pb^{2+}$, and Tris in the concentration of 1 mM. However, in the concentration of 10 mM, almost all metal ions and reagents, except for $Cs^+$, $Li^+$, DTT, and EDTA, inhibited the enzyme activity.

Substrate Specificity of Recombinant PTTS. The recombinant PTTS acted on maltose and trehalose and converted them to each other with the production of a small amount of glucose. It also acted on sucrose and catalyzed the formation of glucose, fructose, and trehalulose [α-D-glucopyranosyl-(1,1)-D-fructofuranose], however, the activity is quite low. In addition, it converted the α,β-1,1-trehalose to maltose, though only about 7% just as with the α,α-1,1-trehalose. No detectable activities were seen with glucose, fructose, galactose, β,β-1,1-trehalose, lactose, mannose, sorbitol, isomaltulose, maltotriose, maltotetraose, maltopentose, starch, or methyl cellulose as substrates under the standard assay conditions described above.

Figure 4:
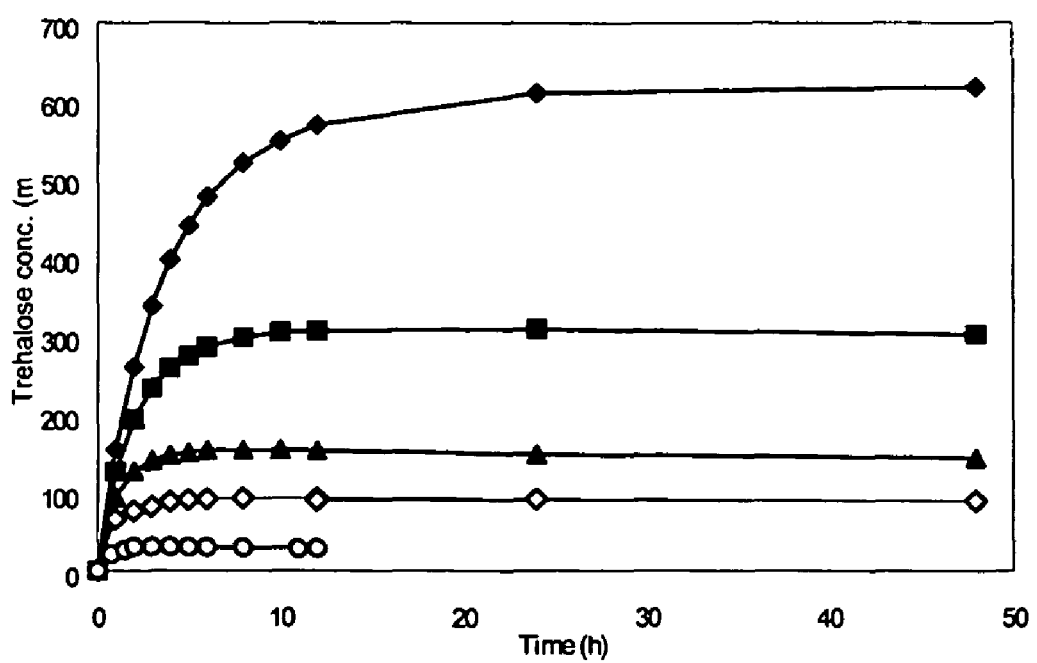
FIG. 4 is a graph which illustrates the effects of substrate concentration on the maximum yield of trehalose by *Picrophilus torridus* trehalose synthase. Purified enzyme was incubated with different concentrations of maltose in 50 mM sodium phosphate buffer (pH 6.0) at 45° C. Samples were collected at various intervals of reaction time and analyzed by HPLC. The symbols which indicated different concentrations of maltose are open square (□) 1 M; solid square (■), 500 mM; solid triangle (▲), 250 mM; open rhombus (◇), 150 mM, and open circle (○), 50 mM.
Figure 5A:
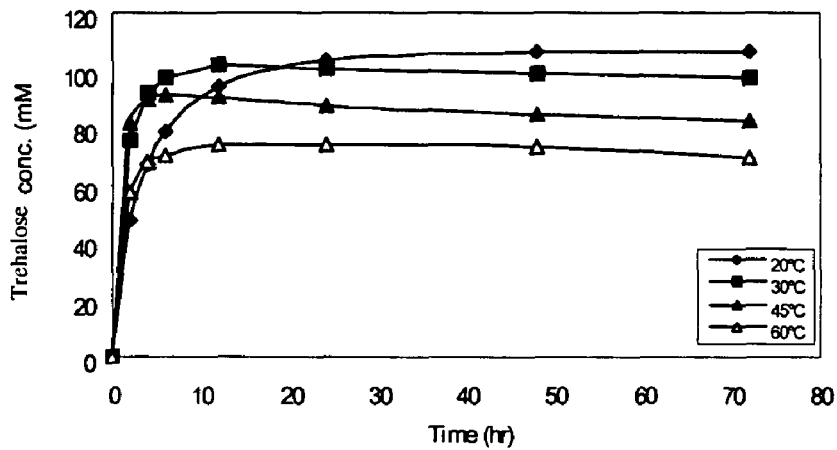
FIG. 5 is a series of graphs illustrating the effects of temperature on the formation of trehalose (5A) and glucose (5B) from maltose (5C) by *Picrophilus torridus* trehalose synthase. Reaction mixtures containing purified *Picrophilus torridus* trehalose synthase, 150 mM maltose and pH 6.0 sodium phosphate buffer were incubated at various temperatures for 72 h. Samples were collected at various intervals and analyzed by HPLC. The symbols which indicated different reaction temperatures are open square (□) denoting temperature of 20° C.; solid square (■) denoting temperature of 30° C.; solid triangle (▲) denoting temperature of 45° C.; and open triangle (Δ) denoting temperature of 0° C.
Figure 5B:
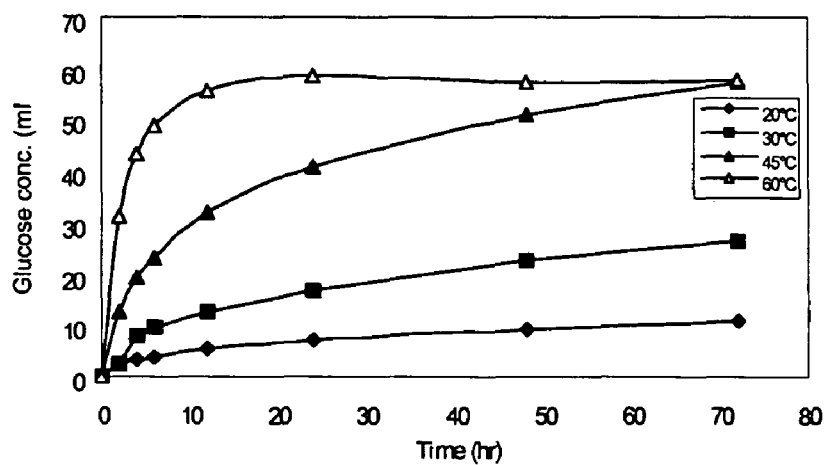
Figure 5C:
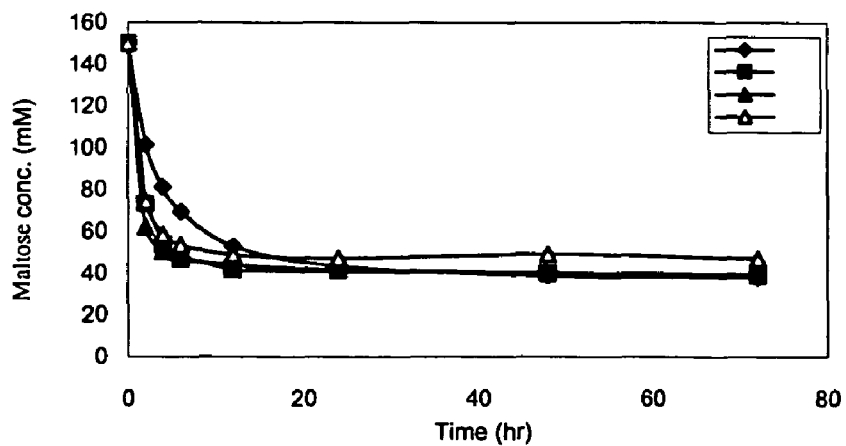

Effects of Substrate Concentration and Temperature on the Maximum Yield of Trehalose. The effects of the substrate concentration on the yield of trehalose by PTTS were examined at pH 6.0, 45° C., and various maltose concentrations. A maximum conversion was reached after 24 hour incubation for each reaction. The final yield of trehalose increased as the substrate concentration increased. The maximum conversions of maltose into trehalose were around 60%, implying that the enzyme conversion rate was independent of the substrate concentration and higher maltose concentration did not have any adverse effect on the trehalose productivity (FIG. 4). For the effects of temperature, reaction mixtures containing 150 mM maltose were incubated under pH 6.0 at 20° C., 30° C., 45° C., or 60° C. for three days and the maximum conversions of maltose into trehalose were 71%, 68%, 61%, and 50% with maltose and glucose contents of 25.4% and 3.6%, 27.6% and 4.3%, 31.2% and 7.8%, and 31.3% and 19.2%, respectively (FIG. 5). Although a faster catalytic rate can be achieved at higher temperature, a slightly lower conversion was displayed due to more glucose generated. Therefore, a higher maximum yield was gained at a lower temperature.

Figure 6:
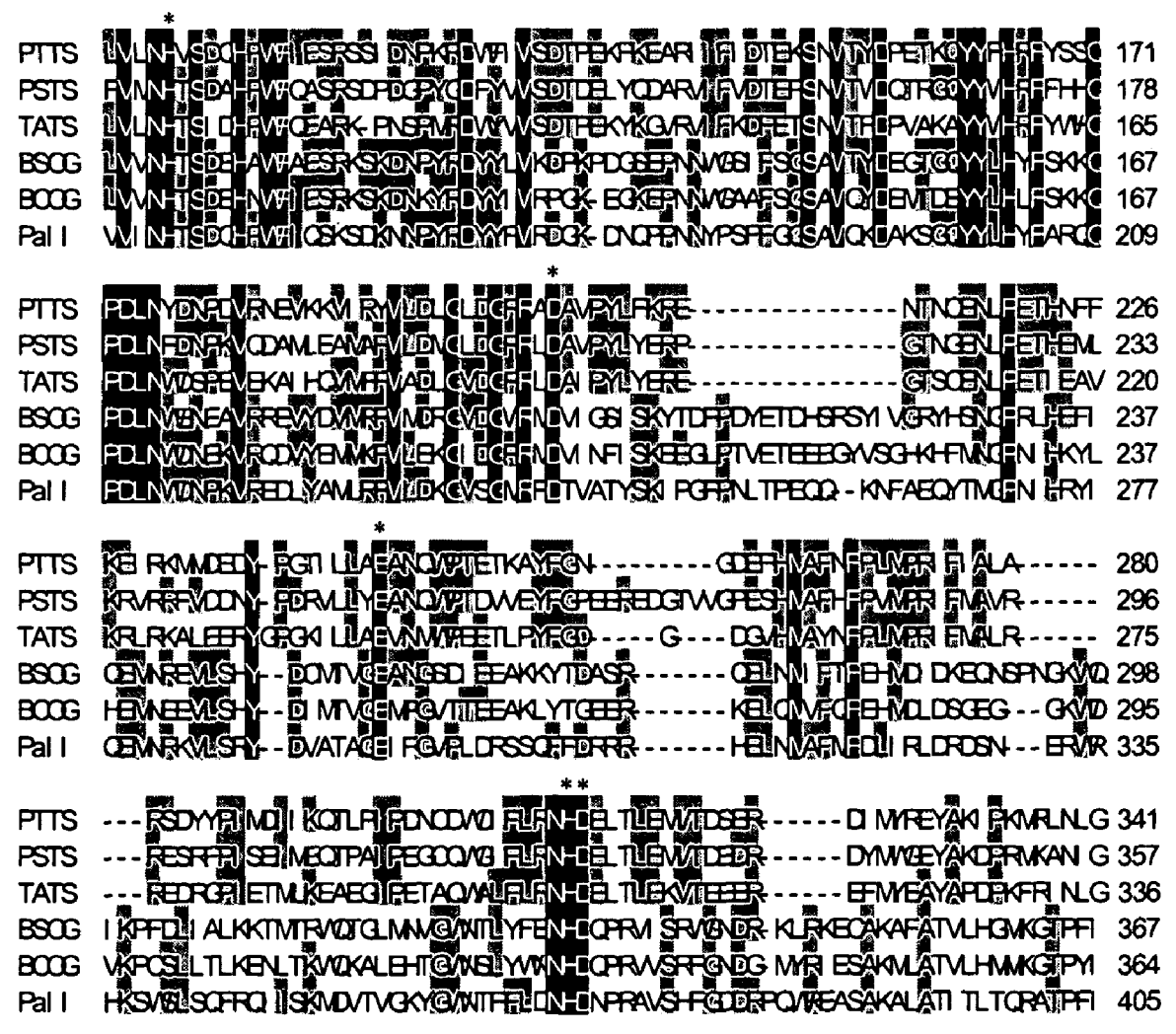

Site-directed Mutagenesis. Domain architectures analysis using the SMART program (http://smart.emble-heidelberg.de) revealed that PTTS contains an α-amylase domain spanning residues 16 to 413, with an E value of 2.10e-107. In alignment with the amino acid sequences of two structure-resolved glycosyl hydrolase family 13 (α-amylase family) enzymes, oligo-1,6-glucosidase from *Bacillus cereus* and isomaltulose synthase from *Klebsiella* sp. LX3, three putative active sites ($Asp^{203}$, $Glu^{245}$, $Asp^{311}$) and two substrate-binding sites ($His^{106}$ and $His^{310}$) of PTTS were deduced (25-26). To verify the importance of these residues, site-directed mutagenesis was used to replace the five residues individually with Ala, and each mutant recombinant protein was purified by Ni-column. The drastic reduction in enzyme activity of all mutants suggested that these five residues might play essential roles in PTTS catalysis (FIG. 9). Moreover, similar conservations of active sites and substrate-binding sites were observed in two other trehalose synthases, *Pimelobacter* trehalose synthase and *Thermus aquaticus* trehalose synthase, further supporting the catalytic importance of these residues in TSase activity (FIG. 6). The information provided by site-directed mutagenesis is significant for the determination of a structure-activity relationship for this enzyme and enables one of ordinary skill in the art to determine which residues can be altered while retaining enzymatic activity.

Discussion

The recombinant PTTS reported here had an optimal pH of 6.0 and optimal temperature of 45° C., and maintained high activity and stability up to pH 5.0 and 60° C. In comparison with other previously reported trehalose synthases, this recombinant PTTS has the most acidic optimum pH. Moreover, the three well-characterized trehalose synthases from *Pimelobacter, T. aquatics*, and *Mycobacterium smegmatis* showed dramatic decreases in enzyme activity at pH below 5.0 and retained lower than 30% of activity (18, 19, 21). However, the PTTS could still maintain 80% of its activity at pH 5.0. Therefore, it is more acid-resistant than other trehalose synthases reported so far. As Maillard reaction, a nonenzymatic protein glycation that often leads to protein denaturation and inactivation, is enhanced with an increase in pH, using enzymes that can tolerate acidic environment could help reduce the chemical reaction of maltose with proteins at high temperature (27-28).

The specific activity of this enzyme toward maltose was estimated to be about 80 units/mg protein, which was about 4.7-fold higher than that of *Pimelobacter* trehalose synthase, about 2.8-fold higher than that of *M. smegmatis* trehalose synthase, roughly equal with that of *P. stutzeri* CJ38 trehalose synthase, and reached about 60% of that of *T. aquaticus* trehalose synthase (18-19, 21, 23). Kinetics analysis showed that the recombinant PTTS had much greater affinity (5 fold) and catalytic efficiency (2.5-fold) for maltose than trehalose. However, the $k_{cat}$ for trehalose was twofold higher than that for maltose (FIG. 8). Since no trehalose gene or other trehalose hydrolyzing genes in the *P. torridus* genome were predicted (NCBI), PTTS might play a regulatory role in controlling the intracellular amount of trehalose itself in *P. torridus*.

The biochemical properties of PTTS without His-tag were the same as that with His-tag. Nevertheless, the specific activity of native PTTS was about 1.3-fold higher than the recombinant His-tag fusion PTTS, perhaps due to the steric hindrance exerted by His-tag that blocks the entrance of substrate into the active site. Though His-tag might have adverse effect on enzyme activity, it facilitates protein purification and simplifies the procedures. The purification yield of PTTS with His-tag was 63%, which was about fourfold higher than that of native protein. Therefore, for applications that require purified enzyme, enzyme with His-tag will be more useful. For applications that use crude enzyme, the enzyme without His-tag should be considered.

Enzymes belonging to the α-amylase family were thought to contain a common structural feature and conserved residues for catalysis and substrate-binding (29). Though trehalose synthase has long been classified as a member of this family and proposed to contain a similar hydrolysis mechanism, no direct evidence or crystal structure can prove this assumption (30). The present invention teaches that these residues of catalytic importance in α-amylase family enzymes were also conserved in PTTS (FIG. 6) and the importance of these residues in PTTS catalysis was revealed in mutagenesis study (FIG. 9). This finding is consistent with previous suggestions and further supported the assumption that PTTS employs a similar hydrolysis mechanism as other α-amylase family enzymes to cleave the α-1,4-glycosidic linkage of maltose. Therefore, a double displacement might proceed through the reaction and $Glu^{245}$ might act as a proton donor and $Asp^{203}$ might act as a nucleophile that attacks the bonded C1 carbon of the maltose. This information is again significant for determining the roles of particular amino acid residues in the catalytic reaction carried out by this enzyme, and therefore for determining which amino acid residues might be modified while retaining enzymatic activity.

More glucose was released when the reaction was performed under a higher temperature (FIG. 5). This phenomenon is likely to be due to the weak hydrolytic property possessed by trehalose synthase itself, which increases as the temperature rises (18-19). However, this could also be explained from the viewpoint of mechanism. As proposed by Koh et al. (30), glucose was generated due to the entry of water molecule into the active site to hydrolyze the enzyme-glucose intermediate prior to the formation of the glycosidic bond. Hence, it is possible that a temperature rise would increase the flexibility of the protein structure, making the active site more accessible to water molecules attacking split glucoses before the formation of the α,α-1,1-glycosidic bond.

In conclusion, the recombinant PTTS of the present invention is thermostable and more acid-resistant than any other trehalose synthases reported so far. Since a high-temperature, acidic environment is unfavorable for the growth of many organisms, the recombinant PTTS can be used to reduce the possibility of contamination. Besides, as high reaction temperature also increases the solubility and fluidity of substrate and no influence was seen on the trehalose conversion by PTTS in high maltose concentration, this enzyme could be applied more economically for the industrial manufacture of trehalose. In addition, inventors of the present invention previously described an enzymatic method that can produce high-maltose syrup and high-protein product simultaneously from raw material such as rice or corn (31-32). Hence, by combining PTTS of the present invention with the previous teachings, a method that enables efficient and economical production of high-value trehalose from low-price crops is developed.

REFERENCES

The following references are specifically applicable to the Examples and to the remainder of the specification and are incorporated herein by reference; these references are referenced in the Examples and in the remainder of the specification by the reference numbers assigned to them.

1. Elbein, A. D.; Pan, Y. T.; Pastuszak, I.; Carroll, D. New insights on trehalose: a multifunctional molecule. *Glycobiology* 2003, 13, 17-27.
2. Brennan, P. J.; Nikaido, H. The envelope of mycobacteria. *Annu. Rev. Biochem.* 1995, 64, 29-63
3. Puech, V.; Chami, M.; Lemassu, A.; Laneelle, M. A.; Schiffler, B.; Gounon, P.; Bayan, N.; Benz, R.; Daffe, M. Structure of the cell envelope of corynebacteria: importance of the non-covalently bound lipids in the formation of the cell wall permeability barrier and fracture plane. *Microbiology* 2001, 147, 1365-1382.
4. Eastmond, P. J.; Graham, I. A. Trehalose metabolism: a regulatory role for trehalose-6-phosphate? *Curr. Opin. Plant Biol.* 2003, 6, 231-235.
5. Gancedo, C.; Flores, C. L. The importance of a functional trehalose biosynthetic pathway for the life of yeasts and fungi. *FEMS Yeast Res.* 2004, 4, 351-359.
6. Wingler, A.; Fritzius, T.; Wiemken, A.; Boller, T.; Aeschbacher, R. A. Trehalose induces the ADP-glucose pyrophosphorylase gene, ApL3, and starch synthesis in Arabidopsis. *Plant Physiol.* 2000, 124, 105-114.
7. Chen, Q.; Behar, K. L.; Xu, T.; Fan, C.; Haddad, G. G. Expression of *Drosophila* trehalose-phosphate synthase in HEK-293 cells increases hypoxia tolerance. *J Biol. Chem.* 2003, 278, 49113-49118.
8. Kandror, O.; DeLeon, A.; Goldberg, A. L. Trehalose synthesis is induced upon exposure of *Escherichia coli* to cold and is essential for viability at low temperatures. *Proc. Natl. Acad. Sci. U.S.A.* 2002, 99, 9727-9732.
9. Purvis, J. E.; Yomano, L. P.; Ingram, L. O. Enhanced trehalose production improves growth of *Escherichia coli* under osmotic stress. *Appl. Environ. Microbiol.* 2005, 71, 3761-3769.
10. Benaroudj, N.; Lee, D. H.; Goldberg, A. L. Trehalose accumulation during cellular stress protects cells and cellular proteins from damage by oxygen radicals. *J Biol. Chem.* 2001, 276, 24261-24267.
11. Welch, W. J.; Brown, C. R. Influence of molecular and chemical chaperones on protein folding. *Cell Stress Chaperones* 1996, 1, 109-115.
12. Schiraldi, C.; Di Lernia, I.; De Rosa, M. Trehalose production: exploiting novel approaches. *Trends Biotechnol.* 2002, 20, 420-425.
13. Cabib, E.; Leloir, L. F.; The biosynthesis of trehalose phosphate. *J. Biol. Chem.* 1958, 231, 259-275.
14. Maruta, K.; Nakada, T.; Kubota, M.; Chaen, H.; Sugimoto, T.; Kurimoto, M.; Tsujisaka, Y. Formation of trehalose from maltooligosaccharides by a novel enzymatic system. *Biosci. Biotechnol. Biochem.* 1995, 59,1829-1834.
15. Nakada, T.; Maruta, K.; Tsusaki, K.; Kubota, M.; Chaen, H.; Sugimoto, T.; Kurimoto, M.; Tsujisaka, Y. Purification and properties of a novel enzyme, maltooligosyl trehalose synthase, from *Arthrobacter* sp. Q36. *Biosci. Biotechnol. Biochem.* 1995, 59, 2210-2214.
16. Nakada, T.; Maruta, K.; Mitsuzumi, H.; Kubota, M.; Chaen, H.; Sugimoto, T.; Kurimoto, M.; Tsujisaka, Y.; Purification and characterization of a novel enzyme, maltooligosyl trehalose trehalohydrolase, from *Arthrobacter* sp. Q36. *Biosci. Biotechnol. Biochem.* 1995, 59, 2215-2218.
17. Nishimoto, T.; Nakano, M.; Ikegami, S.; Chaen, H.; Fukuda, S.; Sugimoto, T.; Kurimoto, M.; Tsujisaka, Y. Existence of a novel enzyme converting maltose into trehalose. *Biosci. Biotechnol. Biochem.* 1995, 59, 2189-2190.
18. Nishimoto, T.; Nakano, M.; Nakada, T.; Chaen, H.; Fukuda, S.; Sugimoto, T.; Kurimoto, M.; Tsujisaka, Y. Purification and properties of a novel enzyme, trehalose sythase, from *Pimelobacter* sp. R48. *Biosci. Biotechnol. Biochem.* 1996, 60, 640-644.
19. Nishimoto, T.; Nakada, T.; Chaen, H.; Fukuda, S.; Sugimoto, T.; Kurimoto, M.; Tsujisaka, Y. Purification and charaterization of a thermostable trehalose synthase from *Thermus aquaticus*. *Biosci. Biotechnol. Biochem.* 1996, 60, 835-839.
20. Koh, S.; Shin, H. J.; Kim, J. S.; Lee, D. S.; Lee, S. Y. Trehalose synthesis from maltose by a thermostable trehalose synthase from *Thermus caldophilus*. *Biotechnology Letters* 1998, 20, 757-761.
21. Pan, Y. T.; Edavana, V. K.; Jourdian, W. J.; Edmondson, R.; Carroll, J. D.; Pastuszak, I.; Elbein, A. D. Trehalose synthase of *Mycobacterium smegmatis*: purification, cloning, expression and properties of the enzyme. *Eur. J. Biochem.* 2004, 271, 4259-4269.
22. Wei, Y. T.; Zhu, Q. X.; Luo, Z. F.; Lu, F. S.; Chen, F. Z.; Wang, 0. Y.; Huang, K.; Meng, J. Z.; Wang, R.; Huang, R. B. Cloning, expression and identification of a new trehalose synthase gene from *Thermobifida fusca* genome. *Acta Biochim. Biophys. Sin.* 2004, 36, 477-484.
23. Lee, J. H.; Lee, K. H.; Kim, C. G.; Lee, S. Y.; Kim, G. J.; Park, Y. H.; Chung, S. O. Cloning and expression of a trehalose synthase from *Pseudomonas stutzeri* CJ38 in *Escherichia coli* for the production of trehalose. *Appl. Microbiol. Biotechnol.* 2005, 68, 213-219.
24. Futterer, O.; Angelov, A.; Liesegang, H.; Gottschalk, G.; Schleper, C.; Schepers, B.; Dock, C.; Antranikian, G.; Liebl, W. Genome sequence of *Picrophilus torridus* and its implications for life around pH 0. *Proc. Natl. Acad. Sci. U.S.A.* 2004, 101, 9091-9096.
25. Watanabe, K.; Miyake, K.; Suzuki, Y. Identification of catalytic and substrate-binding site residues in *Bacillus cereus* ATCC7064 oligo-1,6-glucosidase. *Biosci. Biotechnol. Biochem.* 2001, 65, 2058-2064.
26. Zhang, D.; Li, N.; Lok, S. M.; Zhang, L. H.; Swaminathan, K. Isomaltulose synthase (Pa/I) of *Klebsiella* sp. LX3. Crystal structure and implication of mechanism. *J. Biol. Chem.* 2003, 278, 35428-35434.
27. Dworschak, E. Nonenzyme browning and its effect on protein nutrition. *Crit. Rev. Food. Sci. Nutr.* 1980, 13, 1-40.
28. Fennema, O. R. Carbohydrates. In *Food Chemistry,* 2nd ed.; Marcel Dekker, Inc.: New York, 1985; pp 96-105.
29. MacGregor, E. A.; Janecek, S.; Svensson, B. Relationship of sequence and structure to specificity in the alpha-amylase family of enzymes. *Biochim. Biophys. Acta.* 2001, 1546,1-20.
30. Koh, S.; Kim, J.; Shin, H. J.; Lee, D.; Bae, J.; Kim, D.; Lee, D. S. Mechanistic study of the intramolecular conversion of maltose to trehalose by *Thermus caldophilus* GK24 trehalose synthase. *Carbohydr. Res.* 2003, 338, 1339-1343.
31. Shaw, J. F.; Sheu, J. R. Production of high-maltose syrup and high-protein flour from rice by an enzymatic method. *Biosci. Biotechnol. Biochem.* 1992, 56, 1071-1073.
32. Shaw, J. F. Production of high-maltose syrup and high-protein byproduct from materials that contain start and protein by enzymatic process. 1994, U.S. Pat. No. 5,312,739.

ADVANTAGES OF THE INVENTION AND INDUSTRIAL APPLICABILITY

Nucleic acids and polypeptides according to the invention provide an efficient, rapid, and cost-effective route for the production of large quantities of trehalose, which is of high commercial value. The heat resistant and acid resistant trehalose synthase enzyme of the present invention offers a significant advantage for industrial production of trehalose by increasing the solubility of substrate and reducing the risk of contamination during production.

The interconversion of maltose to trehalose is an industrial process resulting in a commercial and valuable product. Thus, nucleic acids, polypeptides, vectors, host cells, and processes according to the invention have industrial applicability.

With respect to ranges of values, the invention encompasses each intervening value between the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

The publications and patents discussed herein are provided solely for their disclosure prior to the filing date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, literature references, as well as those publications that have been incorporated in those published documents. However, to the extent that any publication incorporated herein by reference refers to information to be published, applicants do not admit that any such information published after the filing date of this application to be prior art.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

We claim:

1. An isolated and purified nucleic acid sequence encoding a functional *Picrophilus torridus* trehalose synthase protein such that the protein has a catalytic activity of catalyzing the intramolecular rearrangement of the α1,4-linkage of maltose to the α1,1-linkage of trehalose, or vice versa, wherein the sequence is a nucleic acid sequence that is at least 99% identical to SEQ ID NO: 1 or SEQ ID NO: 2.

2. The isolated and purified nucleic acid sequence of claim 1 that is DNA.

3. An isolated and purified DNA sequence encoding a functional *Picrophilus torridus* trehalose synthase protein such that the protein has a catalytic activity of catalyzing the intramolecular rearrangement of the α1,4-linkage of maltose to the α1,1-linkage of trehalose, or vice versa, wherein the sequence is selected from the group consisting of:
   (a) SEQ ID NO: 2; and
   (b) a DNA sequence encoding a protein differing by from one to 20 conservative amino acid substitutions from SEQ ID NO: 4, wherein the protein encoded is a functional *Picrophilus torridus* trehalose synthase protein such that the protein has a catalytic activity of catalyzing the intramolecular rearrangement of the α1,4-linkage of maltose to the α1,1-linkage of trehalose, or vice versa, and wherein a conservative amino acid substitution is one of the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu.

4. The isolated and purified DNA sequence of claim 3 wherein the sequence is selected from the group consisting of:
   (a) SEQ ID NO: 2; and
   (b) a DNA sequence encoding a protein differing by from one to 10 conservative amino acid substitutions from SEQ ID NO: 4.

5. The isolated and purified DNA sequence of claim 4 wherein the sequence is selected from the group consisting of:
   (a) SEQ ID NO: 2; and
   (b) a DNA sequence encoding a protein differing by from one to five conservative amino acid substitutions from SEQ ID NO: 4.

6. The isolated and purified DNA sequence of claim 5 wherein the sequence is selected from the group consisting of:
   (a) SEQ ID NO: 2; and
   (b) a DNA sequence encoding a protein differing by from one to two conservative amino acid substitutions from SEQ ID NO: 4.

7. A vector comprising the isolated and purified DNA of claim 4.

8. A host cell transformed or transfected with the vector of claim 7.

9. The host cell of claim 8 that is eukaryotic.

10. The host cell of claim 9 that is a yeast cell.

* * * * *